US007897743B2

(12) United States Patent
Renner et al.

(10) Patent No.: US 7,897,743 B2
(45) Date of Patent: Mar. 1, 2011

(54) HUMANIZED GM-CSF ANTIBODIES

(75) Inventors: Christoph Renner, Homburg (DE); Antony Burgess, Melbourne (AU); Andrew Scott, Melbourne (AU)

(73) Assignee: Ludwig Institute for Cancer Research, New York, NY (US)

( * ) Notice: Subject to any disclaimer, the term of this patent is extended or adjusted under 35 U.S.C. 154(b) by 595 days.

(21) Appl. No.: 12/012,028

(22) Filed: Jan. 31, 2008

(65) Prior Publication Data

US 2010/0167395 A1 Jul. 1, 2010

Related U.S. Application Data

(62) Division of application No. 10/365,123, filed on Feb. 12, 2003, now Pat. No. 7,381,801.

(60) Provisional application No. 60/355,838, filed on Feb. 13, 2002.

(51) Int. Cl.
*C07H 21/04* (2006.01)

(52) U.S. Cl. ..................................................... 536/23.53

(58) Field of Classification Search ........................ None
See application file for complete search history.

(56) References Cited

U.S. PATENT DOCUMENTS 7,381,801 B2 * 6/2008 Renner et al. ............ 530/388.23

* cited by examiner

*Primary Examiner* — Zachary Skelding

(74) *Attorney, Agent, or Firm* — Fulbright & Jaworski LL

(57) ABSTRACT

Chimeric antibodies, as well as fusion proteins which comprise chimeric antibodies, are disclosed. The antibodies bind to GM-CSF, CD-30, and G250 antigen. The fusion proteins include biologically active portions of tumor necrosis factor, or full length tumor necrosis factor. Expression vectors adapted for production of the antibodies, as well as methods for manufacturing these, are also disclosed.

12 Claims, 7 Drawing Sheets

SEQUENCE LISTING

<160> NUMBER OF SEQ ID NOS: 56

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 1
atgaaatgca gctgggtcat sttcttc 27

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 2
atgggatgga gctratcats ytctt 25

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 3
atgaagwtgt ggttaaactg ggttttt 27

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 4
atgractttg wytcagcttg rttt 24

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 5
atggactcca ggctcaamag ttttcctt 28

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
atggctgtcy trgsgctrct cttctgc 27

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 7
atggratgga gckggrtctt tmtctt 26

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 8
atgagagtgc tgattctttt gtg 23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 9
atggmttggg tgtggamctt gctattcctg 30

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 10
atgggcagac ttacattctc attcctg 27

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 11
atggattttg ggctgatttt ttttattg 28

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
atgatggtgt taagtcttct gtacctg 27

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 13
atgaagttgc ctgttaggct gttggtgctg 30

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 14
atggagwcag acacactcct gytatgggt 29

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 15
atgagtgtgc tcactcaggt cctggsgttg 30

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 16
atgaggrccc ctgctcagwt tyttggmwtc ttg 33

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 17
atggatttwc aggtgcagat twtcagcttc 30

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 18
atgaggtkcy ytgytsagyt yctgrgg 27

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 19
atgggcwtca agatggagtc acakwyycwg g 31

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 20
atgtggggay ctktttycmm tttttcaatt g 31

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 21
atggtrtccw casctcagtt ccttg 25

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 22
atgtatatat gtttgttgtc tatttct 27

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 23
atggaagccc cagctcagct tctcttcc 28

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 24
atgaagtttc cttctcaact tctgctc 27

<210> SEQ ID NO 25
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 25

```
tggatggtgg gaagatg                                                  17
```

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 26

```
ccagtggata gacagatg                                                 18
```

<210> SEQ ID NO 27
<211> LENGTH: 456
<212> TYPE: DNA
<213> ORGANISM: Mus musculus
<220> FEATURE:
<223> OTHER INFORMATION: murine 19/2 heavy chain variable region

<400> SEQUENCE: 27

```
atggagctga tcatgctctt cctcctgtca ggaactgcag gcgtccactc              50

tgaggtccag cttcagcagt caggacctga actggtgaaa cctggggcct             100

cagtgaagat atcctgcaag gcttctggat acactttcac tgactacaac             150

atacactggg tgaaacagag ccatggaaag agccttgact ggattggata             200

tattgctcct tacagtggtg gtactggtta caaccaggag ttcaagaaca             250

gggccacatt gactgtagac aaatcctcca gcacagccta catggagctc             300

cgcagtctga catctgatga ctctgcagtc tattactgtg ctagacgaga             350

ccgtttccct tattactttg actactgggg ccaaggcacc cctctcacag             400

tctcctcagc caaaacgaca cccccatctg tctatccact ggcaagggcg             450

aattcc                                                             456
```

<210> SEQ ID NO 28
<211> LENGTH: 139
<212> TYPE: PRT
<213> ORGANISM: Mus musculus
<220> FEATURE:
<223> OTHER INFORMATION: amino acid sequence for murine 19/2 heavy chain variable region

<400> SEQUENCE: 28

```
Met Glu Leu Ile Met Leu Phe Leu Leu Ser Gly Thr Ala Gly Val His
                5                   10                  15

Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
        35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu
65                  70                  75                  80

Phe Lys Asn Arg Ala Thr Leu Thr Val Asp Lys Ser Ser Ser Thr Ala
                85                  90                  95

Tyr Met Glu Leu Arg Ser Leu Thr Ser Asp Asp Ser Ala Val Tyr Tyr
            100                 105                 110
```

```
Cys Ala Arg Arg Asp Arg Phe Pro Tyr Phe Asp Tyr Trp Gly Gln Gly
        115                 120                 125

Thr Thr Leu Arg Val Ser Ser Val Ser Gly Ser
    130                 135


<210> SEQ ID NO 29
<211> LENGTH: 450
<212> TYPE: DNA
<213> ORGANISM: Mus musculus
<220> FEATURE:
<223> OTHER INFORMATION: murine 19/2 light chain variable region

<400> SEQUENCE: 29

atgggcttca agatggagtc acagatccag gtctttgtat acatgttgct            50

gtggttgtct ggtgttgatg gagacattgt gatgatccag tctcaaaaat           100

tcgtatccac atcagtagga gacagggtca atatcacctg caaggccagt           150

cagaatgtgg gaagtaatgt agcctggttg caacagaaac ctggacaatc           200

tcctaaaacg ctgatttact cggcatcgta ccggtccggt cgagtccctg           250

atcgcttcac aggcagtgga tctggaacag atttcattct taccatcact           300

actgtgcagt ctgaagactt ggcagaatat ttctgtcagc aatttaacag           350

gtctcctctc acgttcggtt ctgggaccaa gttggaactg aaacgggctg           400

atgctgcacc aactgtatcc atcttcccac catccagtaa gggcgaattc           450


<210> SEQ ID NO 30
<211> LENGTH: 150
<212> TYPE: PRT
<213> ORGANISM: Mus musculus
<220> FEATURE:
<223> OTHER INFORMATION: amino acid sequence for murine 19/2 light chain
      variable region

<400> SEQUENCE: 30

Met Gly Phe Lys Met Glu Ser Gln Ile Gln Val Phe Val Tyr Met Leu
                5                   10                  15

Leu Trp Leu Ser Gly Val Asp Gly Asp Ile Val Met Ile Gln Ser Gln
            20                  25                  30

Lys Phe Val Ser Thr Ser Val Gly Asp Arg Val Asn Ile Thr Cys Lys
        35                  40                  45

Ala Ser Gln Asn Val Gly Ser Asn Val Ala Trp Leu Gln Gln Lys Pro
    50                  55                  60

Gly Gln Ser Pro Lys Thr Leu Ile Tyr Ser Ala Ser Tyr Arg Ser Gly
65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
            100                 105                 110

Gln Gln Phe Asn Arg Ser Pro Leu Thr Phe Gly Ser Gly Thr Lys Leu
        115                 120                 125

Glu Leu Lys Arg Ala Asp Ala Ala Pro Thr Val Ser Ile Phe Pro Pro
    130                 135                 140

Ser Ser Lys Gly Glu Phe
145                 150


<210> SEQ ID NO 31
<211> LENGTH: 41
<212> TYPE: DNA
```

<213> ORGANISM: Artificial Sequence
<220> FEATURE:
<223> OTHER INFORMATION: primer used for the construction of the chimeric 19/2 light chain

<400> SEQUENCE: 31
catgtttaaa cgccgccacc atgggcttca agatggagtc a 41

<210> SEQ ID NO 32
<211> LENGTH: 38
<212> TYPE: DNA
<213> ORGANISM: Artificial Sequence
<220> FEATURE:
<223> OTHER INFORMATION: primer used for the construction of the chimeric 19/2 light chain

<400> SEQUENCE: 32
agaggatcca ctcacgtttc agttccactt ggtcccag 38

<210> SEQ ID NO 33
<211> LENGTH: 43
<212> TYPE: DNA
<213> ORGANISM: Artificial Sequence
<220> FEATURE:
<223> OTHER INFORMATION: primer used for the construction of the chimeric 19/2 heavy chain

<400> SEQUENCE: 33
catgtttaaa cgccgccacc atggagctga tcatgctctt cct 43

<210> SEQ ID NO 34
<211> LENGTH: 37
<212> TYPE: DNA
<213> ORGANISM: Artificial Sequence
<220> FEATURE:
<223> OTHER INFORMATION: primer used for the construction of the chimeric 19/2 heavy chain

<400> SEQUENCE: 34
agaggatcca ctcacctgag gagactctga gagtggt 37

<210> SEQ ID NO 35
<211> LENGTH: 6159
<212> TYPE: DNA
<213> ORGANISM: Artificial Sequence
<220> FEATURE:
<223> OTHER INFORMATION: pREN 19/2 LC Neo Vector

<400> SEQUENCE: 35
ctcgagagcg ggcagtgagc gcaacgcaat taatgtgagt tagctcactc 50
attaggcacc ccaggcttta cactttatgc tcccggctcg tatgttgtgt 100
ggagattgtg agcggataac aatttcacac agaattcgtg aggctccggt 150
gcccgtcagt gggcagagcg cacatcgccc acagtccccg agaagttggg 200
gggaggggtc ggcaattgaa ccggtgccta gagaaggtgg cgcggggtaa 250
actgggaaag tgatgtcgtg tactggctcc gcctttttcc cgagggtggg 300
ggagaaccgt atataagtgc agtagtcgcc gtgaacgttc tttttcgcaa 350
cgggtttgcc gccagaacac aggtaagtgc cgtgtgtggt tcccgcgggc 400
ctggcctctt tacgggttat ggcccttgcg tgccttgaat tacttccacg 450
cccctggctg cagtacgtga ttcttgatcc cgagcttcgg gttggaagtg 500
ggtgggagag ttcgaggcct tgcgcttaag gagccccttc gcctcgtgct 550

-continued

```
tgagttgagg cctggcctgg gcgctggggc cgccgcgtgc gaatctggtg          600

gcaccttcgc gcctgtctcg ctgctttcga taagtctcta gccatttaaa          650

atttttgatg acctgctgcg acgctttttt tctggcaaga tagtcttgta          700

aatgcgggcc aagatctgca cactggtatt tcggtttttg gggccgcggg          750

cggcgacggg gcccgtgcgt cccagcgcac atgttcggcg aggcggggcc          800

tgcgagcgcg gccaccgaga atcggacggg ggtagtctca agctggccgg          850

cctgctctgg tgcctggcct cgcgccgccg tgtatcgccc cgccctgggc          900

ggcaaggctg gcccggtcgg caccagttgc gtgagcggaa agatggccgc          950

ttcccggccc tgctgcaggg agctcaaaat ggaggacgcg gcgctcggga         1000

gagcgggcgg gtgagtcacc cacacaaagg aaaagggcct ttccgtcctc         1050

agccgtcgct tcatgtgact ccacggagta ccgggcgccg tccaggcacc         1100

tcgattagtt ctcgagcttt tggagtacgt cgtctttagg ttggggggag         1150

gggttttatg cgatggagtt tccccacact gagtgggtgg agactgaagt         1200

taggccagct tggcacttga tgtaattctc cttggaattt gcccttttttg        1250

agtttggatc ttggttcatt ctcaagcctc agacagtggt tcaaagtttt         1300

tttcttccat ttcaggtgta cgcgtctcgg gaagctttag tttaaacgcc         1350

gccacc atg ggc ttc aag atg gag tca cag atc cag gtc ttt         1392
       Met Gly Phe Lys Met Glu Ser Gln Ile Gln Val Phe
                       5                   10

gta tac atg ttg ctg tgg ttg tct ggt gtt gat gga gac att        1434
Val Tyr Met Leu Leu Trp Leu Ser Gly Val Asp Gly Asp Ile
        15                  20                  25

gtg atg atc cag tct caa aaa ttc gta tcc aca tca gta gga        1476
Val Met Ile Gln Ser Gln Lys Phe Val Ser Thr Ser Val Gly
            30                  35                  40

gac agg gtc aat atc acc tgc aag gcc agt cag aat gtg gga        1518
Asp Arg Val Asn Ile Thr Cys Lys Ala Ser Gln Asn Val Gly
                45                  50

agt aat gta gcc tgg ttg caa cag aaa cct gga caa tct cct        1560
Ser Asn Val Ala Trp Leu Gln Gln Lys Pro Gly Gln Ser Pro
55                  60                  65

aaa acg ctg att tac tcg gca tcg tac cgg tcc ggt cga gtc        1602
Lys Thr Leu Ile Tyr Ser Ala Ser Tyr Arg Ser Gly Arg Val
    70                  75                  80

cct gat cgc ttc aca ggc agt gga tct gga aca gat ttc att        1644
Pro Asp Arg Phe Thr Gly Ser Gly Ser Gly Thr Asp Phe Ile
        85                  90                  95

ctt acc atc act act gtg cag tct gaa gac ttg gca gaa tat        1686
Leu Thr Ile Thr Thr Val Gln Ser Glu Asp Leu Ala Glu Tyr
            100                 105                 110

ttc tgt cag caa ttt aac agg tct cct ctc acg ttc ggt tct        1728
Phe Cys Gln Gln Phe Asn Arg Ser Pro Leu Thr Phe Gly Ser
                115                 120

ggg acc aag ttg gaa ctg aaa cgt gagtggatcc atctgggata          1772
Gly Thr Lys Leu Glu Leu Lys Arg
125                 130

agcatgctgt tttctgtctg tccctaacat gccctgtgat tatgcgcaaa         1822

caacacaccc aagggcagaa ctttgttact taaacaccat cctgtttgct         1872

tctttcctca gga act gtg gct gca cca tct gtc ttc atc ttc         1915
               Thr Val Ala Ala Pro Ser Val Phe Ile Phe
                       135                 140
```

-continued

```
ccg cca tct gat gag cag ttg aaa tct gga act gcc tct gtt              1957
Pro Pro Ser Asp Glu Gln Leu Lys Ser Gly Thr Ala Ser Val
        145                 150                 155

gtg tgc ctg ctg aat aac ttc tat ccc aga gag gcc aaa gta              1999
Val Cys Leu Leu Asn Asn Phe Tyr Pro Arg Gly Ala Lys Val
            160                 165                 170

cag tgg aag gtg gat aac gcc ctc caa tcg ggt aac tcc cag              2041
Gln Trp Lys Val Asp Asn Ala Leu Gln Ser Gly Asn Ser Gln
                175                 180

gag agt gtc aca gag cag gac agc aag gac agc acc tac agc              2083
Glu Ser Val Thr Glu Gln Asp Ser Lys Asp Ser Thr Tyr Ser
185                 190                 195

ctc agc agc acc ctg acg ctg agc aaa gca gac tac gag aaa              2125
Leu Ser Ser Thr Leu Thr Leu Ser Lys Ala Asp Tyr Glu Lys
    200                 205                 210

cac aaa gtc tac gcc tgc gaa gtc acc cat cag ggc ctg agc              2167
His Lys Val Tyr Ala Cys Glu Val Thr His Gln Gly Leu Ser
        215                 220                 225

tcg ccc gtc aca aag agc ttc aac agg gga gag tgt tga                  2206
Ser Pro Val Thr Lys Ser Phe Asn Arg Gly Glu Cys
            230                 235

gctagaacta actaactaag ctagcaacgg tttccctcta gcgggatcaa               2256

ttccgccccc ccccctaac gttactggcc gaagccgctt ggaataaggc                2306

cggtgtgcgt ttgtctatat gttattttcc accatattgc cgtcttttgg               2356

caatgtgagg gcccggaaac ctggccctgt cttcttgacg agcattccta               2406

ggggtctttc ccctctcgcc aaaggaatgc aaggtctgtt gaatgtcgtg               2456

aaggaagcag ttcctctgga agcttcttga agacaaacaa cgtctgtagc               2506

gaccctttgc aggcagcgga acccccacc tggcgacagg tgcctctgcg                2556

gccaaaagcc acgtgtataa gatacacctg caaaggcggc acaacccag                2606

tgccacgttg tgagttggat agttgtggaa agagtcaaat ggctctcctc               2656

aagcgtattc aacaaggggc tgaaggatgc ccagaaggta ccccattgta               2706

tgggatctga tctggggcct cggtgcacat gctttacgtg tgtttagtcg               2756

aggttaaaaa acgtctaggc cccccgaacc acggggacgt ggttttcctt               2806

tgaaaaacac gataatacca tggttgaaca agatggattg cacgcaggtt               2856

ctccggccgc ttgggtggag aggctattcg gctatgactg ggcacaacag               2906

acaatcggct gctctgatgc cgccgtgttc cggctgtcag cgcaggggcg               2956

cccggttctt tttgtcaaga ccgacctgtc cggtgccctg aatgaactgc               3006

aggacgaggc agcgcggcta tcgtggctgg ccacgacggg cgttccttgc               3056

gcagctgtgc tcgacgttgt cactgaagcg ggaagggact ggctgctatt               3106

gggcgaagtg ccggggcagg atctcctgtc atctcacctt gctcctgccg               3156

agaaagtatc catcatggct gatgcaatgc ggcggctgca tacgcttgat               3206

ccggctacct gcccattcga ccaccaagcg aaacatcgca tcgagcgagc               3256

acgtactcgg atggaagccg gtcttgtcga tcaggatgat ctggacgaag               3306

agcatcaggg gctcgcgcca gccgaactgt tcgccaggct caaggcgcgc               3356

atgcccgacg gcgaggatct cgtcgtgacc catggcgatg cctgcttgcc               3406

gaatatcatg gtggaaaatg gccgcttttc tggattcatc gactgtggcc               3456

ggctgggtgt ggcggaccgc tatcaggaca tagcgttggc tacccgtgat               3506
```

-continued

```
attgctgaag agcttggcgg cgaatgggct gaccgcttcc tcgtgcttta         3556
cggtatcgcc gctcccgatt cgcagcgcat cgccttctat cgccttcttg         3606
acgagttctt ctgagtcgat cgacctggcg taatagcgaa gaggcccgca         3656
ccgatcgccc ttcccaacag ttgcgcagcc tgaatggcga atgggacgcg         3706
ccctgtagcg gcgcattaag cgcggcgggt gtggtggtta cgcgcagcgt         3756
gaccgctaca cttgccagcg ccctagcgcc cgctcctttc gctttcttcc         3806
cttcctttct cgccacgttc gccggctttc cccgtcaagc tctaaatcgg         3856
gggctccctt tagggttccg atttagtgct ttacggcacc tcgaccccaa         3906
aaaacttgat tagggtgatg gttcacgtag tgggccatcg ccctgataga         3956
cggtttttcg ccctttgacgt tggagtccac gttctttaat agtggactct        4006
tgttccaaac tggaacaaca ctcaacccta tctcggtcta tttataaggg         4056
attttgccga tttcggccta ttggttaaaa aatgagctga tttaacaaaa         4106
tttaacgcga attttaacaa aatattaacg cttacaattt aggtggcact         4156
tttcggggaa atgtgcgcgg aacccctata tttgtttatt tttctaaata         4206
cattcaaata tgtatccgct catgagacaa taaccctgat aaatgcttca         4256
ataatattga aaaaggaaga gtatgagtat tcaacatttc cgtgtcgccc         4306
ttattccctt ttttgcggca ttttgcctta ctgtttttgc tcacccagaa         4356
acgctggtga aagtaaaaga tgctgaagat cagttgggtg cacgagtggg         4406
ttacatcgaa ctggatctca acagcggtaa gatccttgag agttttcgcc         4456
ccgaagaacg ttttccaatg atgagcactt ttaaagttct gctatgtggc         4506
gcggtattat cccgtattga cgccgggcaa gagcaactcg gtcgccgcat         4556
acactattct cagaatgact tggttgagta ctcaccagtc acagaaaagc         4606
atattacgga tggcatgaca gtaagagaat tatgcagtgc tgccataacc         4656
atgagtgata acactgcggc caacttactt ctgacaacga tcggaggacc         4706
gaaggagcta accgcttttt tgcacaacat gggggatcat gtaactcgcc         4756
ttgatcgttg ggaaccggag ctgaatgaag ccataccaaa cgacgagcgt         4806
gacaccacga tgcctgtagc aatggcaaca acgttgcgca aactattaac         4856
tggcgaacta cttactctag cttcccggca acaattaata gactggatgg         4906
aggcggataa agttgcagga ccacttctgc gctcggccct tccggctggc         4956
tggtttattg ctgataaatc tggagccggt gagcgtgggt ctcgcggtat         5006
cattgcagca ctggggccag atggtaagcc ctcccgtatc gtagttatct         5056
acacgacggg gagtcaggca actatggatg aacgaaatag acagatcgct         5106
gagataggtg cctcactgat taagcattgg taactgtcag accaagttta         5156
ctcatatata ctttagattg atttaaaact tcatttttaa tttaaaagga         5206
tctaggtgaa gatccttttt gataatctca tgaccaaaat cccttaacgt         5256
gagttttcgt tccactgagc gtcagacccc gtagaaaaga tcaaaggatg         5306
ttcttgagat cctttttttc tgcacgtaat ctgctgcttg caaacaaaaa         5356
accaccgcta ccagcggtgg tttgtttgcc ggatcaagag ctaccaactc         5406
tttttccgaa ggtaactggc ttcagcagag cgcagatacc aaatactgtc         5456
cttctagtgt agccgtagtt aggccaccac ttcaagaact ctgtagcacc         5506
```

```
gcctacatac ctcgctctgc taatcctgtt accagtggct gctgccagtg      5556

gcgataagtc gtgtcttacc gggttggact caagacgata gttaccggat      5606

aaggcgcagc ggtcgggctg aacggggggt tcgtgcacac agcccagctt      5656

ggagcgaacg acctacaccg aactgagata cctacagcgt gagctatgag      5706

aaagcgccac gcttcccgaa gggagaaagg cggacaggta tccggtaagc      5756

ggcagggtcg gaacaggaga gcgcacgagg gagcttccag ggggaaacgc      5806

ctggtatctt tatagtcctg tcgggtttcg ccacctctga cttgagcgtc      5856

gatttttgtg atgctcgtca ggggggcgga gcctatggaa aaacgccagc      5906

aacgcggcct ttttacggtt cctggccttt tgctggcctt ttgctcacat      5956

gttctttcct gcgttatccc ctgattctgt ggataaccgt attaccgcct      6006

ttgagtgagc tgataccgct cgccgcagcc gaacgaccga gcgcagcgag      6056

tcagtgagcg aggaagcgga agagcgccca atacgcaaac cgcctctccc      6106

cgcgcgttgg ccgattcatt aatgcaggta tcacgaggcc ctttcgtctt      6156

cac                                                         6159


<210> SEQ ID NO 36
<211> LENGTH: 6579
<212> TYPE: DNA
<213> ORGANISM: Artificial Sequence
<220> FEATURE:
<223> OTHER INFORMATION: pREN 19/2 HC DHFR Vector

<400> SEQUENCE: 36

ctcgagagcg ggcagtgagc gcaacgcaat taatgtgagt tagctcactc        50

attaggcacc ccaggcttta cactttatgc tcccggctcg tatgttgtgt       100

ggagattgtg agcggataac aatttcacac agaattcgtg aggctccggt       150

gcccgtcagt gggcagagcg cacatcgccc acagtccccg agaagttggg       200

gggaggggtc ggcaattgaa ccggtgccta gagaaggtgg cgcggggtaa       250

actgggaaag tgatgtcgtg tactggctcc gcctttttcc cgagggtggg       300

ggagaaccgt atataagtgc agtagtcgcc gtgaacgttc tttttcgcaa       350

cgggtttgcc gccagaacac aggtaagtgc cgtgtgtggt tcccgcgggc       400

ctggcctctt tacgggttat ggcccttgcg tgccttgaat tacttccacg       450

ggtgggagag ttcgaggcct tgcgcttaag gagccccttc gcctcgtgct       500

tgagttgagg cctggcctgg gcgctggggc cgccgcgtgc gaatctggtg       550

gcaccttcgc gcctgtctcg ctgctttcga taagtctcta gccatttaaa       600

atttttgatg acctgctgcg acgctttttt tctggcaaga tagtcttgta       650

aatgcgggcc aagatctgca cactggtatt tcggtttttg gggccgcggg       700

cggcgacggg gcccgtgcgt cccagcgcac atgttcggcg aggcggggcc       750

tgcgagcgcg gccaccgaga atcggacggg ggtagtctca agctggccgg       800

cctgctctgg tgcctggcct cgcgccgccg tgtatcgccc cgccctgggc       850

ggcaaggctg gcccggtcgg caccagttgc gtgagcggaa agatggccgc       900

ttcccggccc tgctgcaggg agctcaaaat ggaggacgcg gcgctcggga       950

gagcgggcgg gtgagtcacc cacacaaagg aaaagggcct ttccgtcctc      1000

agccgtcgct tcatgtgact ccacggagta ccgggcgccg tccaggcacc      1050
```

```
tcgattagtt ctcgagcttt tggagtacgt cgtctttagg ttggggggag              1100

gggttttatg cgatggagtt tccccacact gagtgggtgg agactgaagt              1150

taggccagct tggcacttga tgtaattctc cttggaattt gcccttttg               1200

agtttggatc ttggttcatt ctcaagcctc agacagtggt tcaaagtttt              1250

tttcttccat ttcaggtgta cgcgtctcgg gaagctttag tttaaacgcc              1300

gccacc atg gag ctg atc atg ctc ttc ctc ctg tca gga act              1342
       Met Glu Leu Ile Met Leu Phe Leu Leu Ser Gly Thr
                       5                  10

gca ggc gtc cac tct gag gtc cag ctt cag cag tca gga cct              1384
Ala Gly Val His Ser Glu Val Gln Leu Gln Gln Ser Gly Pro
        15                  20                  25

gaa ctg gtg aaa cct ggg gcc tca gtg aag ata tcc tgc aag              1426
Glu Leu Val Lys Pro Gly Ala Ser Val Lys Ile Ser Cys Lys
            30                  35                  40

gct tct gga tac act ttc act gac tac aac ata cac tgg gtg              1468
Ala Ser Gly Tyr Thr Phe Thr Asp Tyr Asn Ile His Trp Val
                45                  50

aaa cag agc cat gga aag agc ctt gac tgg att gga tat att              1510
Lys Gln Ser His Gly Lys Ser Leu Asp Trp Ile Gly Tyr Ile
55                  60                  65

gct cct tac agt ggt ggt act ggt tac aac cag gag ttc aag              1552
Ala Pro Tyr Ser Gly Gly Thr Gly Tyr Asn Gln Glu Phe Lys
    70                  75                  80

aac agg gcc aca ttg act gta gac aaa tcc tcc agc aca gcc              1594
Asn Arg Ala Thr Leu Thr Val Asp Lys Ser Ser Ser Thr Ala
        85                  90                  95

tac atg gag ctc cgc agt ctg aca tct gat gac tct gca gtc              1636
Tyr Met Glu Leu Arg Ser Leu Thr Ser Asp Asp Ser Ala Val
            100                 105                 110

tat tac tgt gct aga cga gac cgt ttc cct tat tac ttt gac              1678
Tyr Tyr Cys Ala Arg Arg Asp Arg Phe Pro Tyr Tyr Phe Asp
                115                 120

tac tgg ggc caa ggc acc act ctc aga gtc tcc tca gtg agt              1720
Tyr Trp Gly Gln Gly Thr Thr Leu Arg Val Ser Ser
125                 130                 135

ggatcctctg cgcctgggcc cagctctgtc ccacaccgcg gtcacatggc              1770

accacctctc ttgcagcc tcc acc aag ggc cca tcg gtc ttc                 1812
                    Ser Thr Lys Gly Pro Ser Val Phe
                                140

ccc ctg gca ccc tcc tcc aag agc acc tct ggg ggc aca                  1851
Pro Leu Ala Pro Ser Ser Lys Ser Thr Ser Gly Gly Thr
145                 150                 155

gcg gcc ctg ggc tgc ctg gtc aag gac tac ttc ccc gaa ccg              1893
Ala Ala Leu Gly Cys Leu Val Lys Asp Tyr Phe Pro Glu Pro
        160                 165                 170

gtg acg gtg tcg tgg aac tca ggc gcc ctg acc agc ggc gtg              1935
Val Thr Val Ser Trp Asn Ser Gly Ala Lys Thr Ser Gly Val
            175                 180                 185

cac acc ttc ccg gct gtc cta cag tcc tca gga ctc tac tcc              1977
His Thr Phe Pro Ala Val Leu Gln Ser Ser Gly Leu Tyr Ser
                190                 195

ctc agc agc gtg gtg acc gtg ccc tcc agc agc ttg ggc acc              2019
Leu Ser Ser Val Val Ser Val Pro Ser Ser Ser Leu Gly Thr
200                 205                 210

cag acc tac atc tgc aac gtg aat cac aag ccc agc aac acc              2061
Gln Thr Tyr Ile Cys Asn Val Asn His Lys Pro Ser Asn Thr
    215                 220                 225
```

```
aag gtg gac aag aaa gtt gag ccc aaa tct tgt gac aaa act            2103
Lys Val Asn Lys Lys Val Glu Pro Lys Ser Cys Asn Lys Thr
        230                 235                 240

cac aca tgc cca ccg tgc cca gca cct gaa ctc ctg ggg gga            2145
His Thr Cys Pro Pro Cys Pro Ala Pro Glu Leu Leu Gly Gly
            245                 250                 255

ccg tca gtc ttc ctc ttc ccc cca aaa ccc aag gac acc ctc            2187
Pro Ser Val Phe Leu Phe Pro Pro Lys Pro Lys Asn Thr Leu
                260                 265

atg atc tcc cgg acc cct gag gtc aca tgc gtg gtg gtg gac            2229
Met Ile Ser Arg Thr Pro Glu Val Thr Cys Val Val Val Asn
270                 275                 280

gtg agc cac gaa gac cct gag gtc aag ttc aac tgg tac gtg            2271
Val Ser His Glu Asn Pro Glu Val Lys Phe Asn Trp Tyr Val
    285                 290                 295

gac ggc gtg gag gtg cat aac gcc aag aca aag ccg cgg gag            2313
Asp Gly Val Glu Val His Asn Ala Lys Thr Lys Pro Arg Glu
        300                 305                 310

gag cag tac aac agc acg tac cgg gtg gtc agc gtc ctc acc            2355
Glu Gln Tyr Asn Ser Thr Tyr Arg Val Val Ser Val Leu Thr
            315                 320                 325

gtc ctg cac cag gac tgg ctg aat ggc aag gag tac aag tgc            2397
Val Leu His Gln Asp Trp Leu Asn Gly Lys Glu Tyr Lys Cys
                330                 335

aag gtc tcc aac aaa gcc ctc cca gcc ccc atc gag aaa acc            2439
Lys Val Ser Asn Lys Ala Leu Pro Ala Pro Ile Glu Lys Thr
340                 345                 350

atc tcc aaa gcc aaa ggg cag ccc cga gaa cca cag gtg tac            2481
Ile Ser Lys Ala Lys Gly Gln Pro Arg Glu Pro Gln Val Tyr
    355                 360                 365

acc ctg ccc cca tcc cgg gag gag atg acc aag aac cag gtc            2523
Thr Leu Pro Pro Ser Arg Glu Glu Met Thr Lys Asn Gln Val
        370                 375                 380

agc ctg acc tgc ctg gtc aaa ggc ttc tat ccc agc gac atc            2565
Ser Leu Thr Cys Leu Val Lys Gly Phe Tyr Pro Ser Asn Ile
            385                 390                 395

gcc gtg gag tgg gag agc aat ggg cag ccg gag aac aac tac            2607
Ala Val Glu Trp Glu Ser Asn Gly Gln Pro Glu Asn Asn Tyr
                400                 405

aag acc acg cct ccc gtg ctg gac tcc gac ggc tcc ttc ttc            2649
Lys Thr Thr Pro Pro Val Leu Asp Ser Asp Gly Ser Phe Phe
410                 415                 420

ctc tac agc aag ctc acc gtg gac aag agc agg tgg cag cag            2691
Leu Tyr Ser Lys Leu Thr Val Asp Lys Ser Arg Trp Gln Gln
    425                 430                 435

ggg aac gtc ttc tca tgc tcc gtg atg cat gag gct ctg cac            2733
Gly Asn Val Phe Ser Cys Ser Val Met His Glu Ala Leu His
        440                 445                 450

aac cac tac acg cag aag agc ctc tcc ctg tct ccg ggt aaa            2775
Asn His Tyr Thr Gln Lys Ser Leu Ser Leu Ser Pro Gly Lys
            455                 460                 465

tga gctagaaact aactaagcta gcaacggttt ccctctagcg ggatcaattc         2828

cgcccccccc ccctaacgtt actggccgaa gccgcttgga ataaggccgg             2878

tgtgcgtttg tctatatgtt attttccacc atattgccgt cttttggcaa             2928

tgtgagggcc cggaaacctg gccctgtctt cttgacgagc attcctaggg             2978

gtctttcccc tctcgccaaa ggaatgcaag gtctgttgaa tgtcgtgaag             3028

gaagcagttc ctctggaagc ttcttgaaga caaacaacgt ctgtagcgac             3078
```

-continued

```
cctttgcagg cagcggaacc ccccacctgg cgacaggtgc ctctgcggcc    3128
aaaagccacg tgtataagat acacctgcaa aggcggcaca accccagtgc    3178
cacgttgtga gttggatagt tgtggaaaga gtcaaatggc tctcctcaag    3228
cgtattcaac aaggggctga aggatgccca gaaggtaccc cattgtatgg    3278
gatctgatct ggggcctcgg tgcacatgct ttacgtgtgt ttagtcgagg    3328
ttaaaaaacg tctaggcccc ccgaaccacg gggacgtggt tttcctttga    3378
aaaacacgat aataccatgg ttcgaccatt gaactgcatc gtcgccgtgt    3428
cccaaaatat ggggattggc aagaacggag acctaccctg gcctccgctc    3478
aggaacgagt tcaagtactt ccaaagaatg accacaacct cttcagtgga    3528
aggtaaacag aatctggtga ttatgggtag gaaaacctgg ttctccattc    3578
ctgagaagaa tcgaccttta aaggacagaa ttaatggttc gatatagttc    3628
tcagtagaga actcaaagaa ccaccacgag gagctcattt tcttgccaaa    3678
agtttggatg atgccttaag acttattgaa caaccggaat tggcaagtaa    3728
agtagacatg gtttggatag tcggaggcag ttctgtttac caggaagcca    3778
tgaatcaacc aggccacctc agactctttg tgacaaggat catgcaggaa    3828
tttgaaagtg acacgttttt cccagaaatt gatttgggga aatataaact    3878
tctcccagaa tacccaggcg tcctctctga ggtccaggag gaaaaaggca    3928
tcaagtataa gtttgaagtc tacgagaaga aagactaaca ggaagatgct    3978
ttcaagttct ctgctcccct cctaaagcta tgcattttta taagaccatg    4028
ggacttttgc tggtcgatcg acctggcgta atagcgaaga ggcccgcacc    4078
gatcgccctt cccaacagtt gcgcagcctg aatggcgaat gggacgcgcc    4128
ctgtagcggc gcattaagcg cggcgggtgt ggtggttacg cgcagcgtga    4178
ccgctacact tgccagcgcc ctagcgcccg ctcctttcgc tttcttccct    4228
tcctttctcg ccacgttcgc cggctttccc cgtcaagctc taaatcgggg    4278
gctcccttta gggttccgat ttagtgcttt acggcacctc gaccccaaaa    4328
aacttgatta gggtgatggt tcacgtagtg ggccatcgcc ctgatagacg    4378
gtttttcgcc tttgacgttg gagtccacgt tctttaatag tggactcttg    4428
ttccaaactg gaacaacact caaccctatc tcggtctatt tataagggat    4478
tttgccgatt tcggcctatt ggttaaaaaa tgagctgatt taacaaaatt    4528
taacgcgaat tttaacaaaa tattaacgct tacaatttag gtggcacttt    4578
tcggggaaat gtgcgcggaa cccctatatt tgtttatttt tctaaataca    4628
ttcaaatatg tatccgctca tgagacaata accctgataa atgcttcaat    4678
aatattgaaa aaggaagagt atgagtattc aacatttccg tgtcgccctt    4728
attccctttt ttgcggcatt ttgccttact gtttttgctc acccagaaac    4778
gctggtgaaa gtaaaagatg ctgaagatca gttgggtgca cgagtgggtt    4828
acatcgaact ggatctcaac agcggtaaga tccttgagag ttttcgcccc    4878
gaagaacgtt ttccaatgat gagcactttt aaagttctgc tatgtggcgc    4928
ggtattatcc cgtattgacg ccgggcaaga gcaactcggt cgccgcatac    4978
actattctca gaatgacttg gttgagtact caccagtcac agaaaagcat    5028
attacggatg gcatgacagt aagagaatta tgcagtgctg ccataaccat    5078
```

```
gagtgataac actgcggcca acttacttct gacaacgatc ggaggaccga        5128

aggagctaac cgcttttttg cacaacatgg gggatcatgt aactcgcctt        5178

gatcgttggg aaccggagct gaatgaagcc ataccaaacg acgagcgtga        5228

caccacgatg cctgtagcaa tggcaacaac gttgcgcaaa ctattaactg        5278

gcgaactact tactctagct tcccggcaac aattaataga ctggatggag        5328

gcggataaag ttgcaggacc acttctgcgc tcggcccttc cggctggctg        5378

gtttattgct gataaatctg gagccggtga gcgtgggtct cgcggtatca        5428

ttgcagcact ggggccagat ggtaagccct cccgtatcgt agttatctac        5478

acgacgggga gtcaggcaac tatggatgaa cgaaatagac agatcgctga        5528

gataggtgcc tcactgatta agcattggta actgtcagac caagtttact        5578

catatatact ttagattgat ttaaaacttc atttttaatt taaaaggatc        5628

taggtgaaga tcctttttga taatctcatg accaaaatcc cttaacgtga        5678

gttttcgttc cactgagcgt cagaccccgt agaaaagatc aaaggatgtt        5728

cttgagatcc tttttttctg cacgtaatct gctgcttgca aacaaaaaac        5778

caccgctacc agcggtggtt tgtttgccgg atcaagagct accaactctt        5828

tttccgaagg taactggctt cagcagagcg cagataccaa atactgtcct        5878

tctagtgtag ccgtagttag gccaccactt caagaactct gtagcaccgc        5928

ctacatacct cgctctgcta atcctgttac cagtggctgc tgccagtggc        5978

gataagtcgt gtcttaccgg gttggactca agacgatagt taccggataa        6028

ggcgcagcgg tcgggctgaa cggggggttc gtgcacacag cccagcttgg        6078

agcgaacgac ctacaccgaa ctgagatacc tacagcgtga gctatgagaa        6128

agcgccacgc ttcccgaagg gagaaaggcg gacaggtatc cggtaagcgg        6178

cagggtcgga acaggagagc gcacgaggga gcttccaggg ggaaacgcct        6228

ggtatcttta tagtcctgtc gggtttcgcc acctctgact tgagcgtcga        6278

tttttgtgat gctcgtcagg ggggcggagc ctatggaaaa acgccagcaa        6328

cgcggccttt ttacggttcc tggccttttg ctggcctttt gctcacatgt        6378

tctttcctgc gttatcccct gattctgtgg ataaccgtat taccgccttt        6428

gagtgagctg ataccgctcg ccgcagccga acgaccgagc gcagcgagtc        6478

agtgagcgag gaagcggaag agcgcccaat acgcaaaccg cctctccccg        6528

cgcgttggcc gattcattaa tgcaggtatc acgaggccct ttcgtcttca        6578

c                                                             6579


<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37

ttcttgaagt ctggtgatgc tgcc                                      24


<210> SEQ ID NO 38
<211> LENGTH: 31
<212> TYPE: DNA
<213> ORGANISM: Artificial Sequence
<220> FEATURE:
```

<223> OTHER INFORMATION: primer

<400> SEQUENCE: 38
caagctagcc ctctaagact cctcccctgt t 31

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
gaactcgagt catttacccg gagacaggga gag 33

<210> SEQ ID NO 40
<211> LENGTH: 32
<212> TYPE: DNA
<213> ORGANISM: Artificial Sequence
<220> FEATURE:
<223> OTHER INFORMATION: primer

<400> SEQUENCE: 40
gcgccatggc ccaggtgcaa ctgcagcagt ca 32

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
cagggatcca ctcacctgag gagacggtga ccgt 34

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
agcgccatgg acatcgagct cactcagtct cca 33

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43
cagggatcca actcacgttt gatttccagc ttggt 35

<210> SEQ ID NO 44
<211> LENGTH: 465
<212> TYPE: DNA
<213> ORGANISM: Mus Musculus
<220> FEATURE:
<223> OTHER INFORMATION: nucleotide sequence of murine heavy chain variable region

<400> SEQUENCE: 44
gtttaaacgc cgccaccatg aactggacct ggaccgtgtt ttgcctgctc 50
gctgtggctc ctggggccca cagcgccatg gcccaggtgc aactgcagca 100

```
gtcaggggct gagctggcta gacctggggc ttcagtgaag atgtcctgca              150

aggcttctgg ctacaccttt actacctaca caatacactg ggtaagacag              200

aggcctggac acgatctgga atggattgga tacattaatc ctagcagtgg              250

atattctgac tacaatcaaa gcttcaaggg caagaccaca ttgactgcag              300

acaagtcctc caacacagcc tacatgcaac tgaacagcct gacatctgag              350

gactctgcgg tctattactg tgcaagaaga gcggactatg gtaactacga              400

atatacctgg tttgcttact ggggccaagg gaccacggtc accgtctcct              450

caggtgagtg gatcc                                                    465


<210> SEQ ID NO 45
<211> LENGTH: 145
<212> TYPE: PRT
<213> ORGANISM: Mus musculus
<220> FEATURE:
<223> OTHER INFORMATION: amino acid sequence for murine heavy chain
      variable region

<400> SEQUENCE: 45

Met Asn Trp Thr Trp Thr Val Phe Cys Leu Leu Ala Val Ala Pro Gly
                5                   10                  15

Ala His Ser Ala Met Ala Gln Val Gln Leu Gln Gln Ser Gly Ala Glu
            20                  25                  30

Leu Ala Arg Pro Gly Ala Ser Val Lys Met Ser Cys Lys Ala Ser Gly
        35                  40                  45

Tyr Thr Phe Thr Thr Tyr Thr Ile His Trp Val Arg Gln Arg Pro Gly
    50                  55                  60

His Asp Leu Glu Trp Ile Gly Tyr Ile Asn Pro Ser Ser Gly Tyr Ser
65                  70                  75                  80

Asp Tyr Asn Gln Ser Phe Lys Gly Lys Thr Thr Leu Thr Ala Asp Lys
                85                  90                  95

Ser Ser Asn Thr Ala Tyr Met Gln Leu Asn Ser Leu Thr Ser Glu Asp
            100                 105                 110

Ser Ala Val Tyr Tyr Cys Ala Arg Arg Ala Asp Tyr Gly Asn Tyr Glu
        115                 120                 125

Tyr Thr Trp Phe Ala Tyr Trp Gly Gln Gly Thr Thr Val Thr Val Ser
    130                 135                 140

Ser
145


<210> SEQ ID NO 46
<211> LENGTH: 415
<212> TYPE: DNA
<213> ORGANISM: Mus musculus
<220> FEATURE:
<223> OTHER INFORMATION: nucleotide sequence for murine light chain
      variable region

<400> SEQUENCE: 46

gtttaaacgc cgccaccatg aactggacct ggaccgtgtt ttgcctgctc               50

gctgtggctc ctggggccca cagcgccatg gacatcgagc tcactcagtc              100

tccaaaattc atgtccacat cagtaggaga cagggtcaac gtcacctaca              150

aggccagtca gaatgtgggt actaatgtag cctggtttca acaaaaacca              200

gggcaatctc ctaaagttct gatttactcg gcatcttacc gatacagtgg              250

agtccctgat cgcttcacag gcagtggatc tggaacagat ttcactctca              300
```

```
ccatcagcaa tgtgcagtct gaagacttgg cagagtattt ctgtcagcaa          350

tatcacacct atcctctcac gttcggaggg ggcaccaagc tggaaatcaa          400

acgtgagttg gatcc                                                415
```

<210> SEQ ID NO 47
<211> LENGTH: 129
<212> TYPE: PRT
<213> ORGANISM: Mus musculus
<220> FEATURE:
<223> OTHER INFORMATION: amino acid sequence for murine light chain variable region

<400> SEQUENCE: 47

```
Met Asn Trp Thr Trp Thr Val Phe Cys Leu Leu Ala Val Ala Pro Gly
                5                   10                  15

Ala His Ser Ala Met Asp Ile Glu Leu Thr Gln Ser Pro Lys Phe Met
            20                  25                  30

Ser Thr Ser Val Gly Asp Arg Val Asn Val Thr Tyr Lys Ala Ser Gln
        35                  40                  45

Asn Val Gly Thr Asn Val Ala Trp Phe Gln Gln Lys Pro Gly Gln Ser
    50                  55                  60

Pro Lys Val Leu Ile Tyr Ser Ala Ser Tyr Arg Tyr Ser Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Glu Tyr Phe Cys Gln Gln Tyr
            100                 105                 110

His Thr Tyr Pro Leu Thr Phe Gly Gly Gly Thr Lys Leu Glu Ile Lys
        115                 120                 125

Arg
```

<210> SEQ ID NO 48
<211> LENGTH: 5759
<212> TYPE: DNA
<213> ORGANISM: Artificial Sequence
<220> FEATURE:
<223> OTHER INFORMATION: Light chain expression vector pREN-Neo.

<400> SEQUENCE: 48

```
ctcgagagcg ggcagtgagc gcaacgcaat taatgtgagt tagctcactc           50

attaggcacc ccaggcttta cactttatgc tcccggctcg tatgttgtgt          100

ggagattgtg agcggataac aatttcacac agaattcgtg aggctccggt          150

gcccgtcagt gggcagagcg cacatcgccc acagtccccg agaagttggg          200

gggaggggtc ggcaattgaa ccggtgccta gagaaggtgg cgcggggtaa          250

actgggaaag tgatgtcgtg tactggctcc gcctttttcc cgagggtggg          300

ggagaaccgt atataagtgc agtagtcgcc gtgaacgttc tttttcgcaa          350

cgggtttgcc gccagaacac aggtaagtgc cgtgtgtggt tcccgcgggc          400

ctggcctctt tacgggttat ggcccttgcg tgccttgaat tacttccacg          450

cccctggctg cagtacgtga ttcttgatcc cgagcttcgg gttggaagtg          500

ggtgggagag ttcgaggcct tgcgcttaag gagccccttc gcctcgtgct          550

tgagttgagg cctggcctgg gcgctggggc cgccgcgtgc gaatctggtg          600

gcaccttcgc gcctgtctcg ctgctttcga taagtctcta gccatttaaa          650
```

```
atttttgatg acctgctgcg acgctttttt tctggcaaga tagtcttgta          700

aatgcgggcc aagatctgca cactggtatt tcggtttttg gggccgcggg          750

cggcgacggg gcccgtgcgt cccagcgcac atgttcggcg aggcggggcc          800

tgcgagcgcg gccaccgaga atcggacggg ggtagtctca agctggccgg          850

cctgctctgg tgcctggcct cgcgccgccg tgtatcgccc cgccctgggc          900

ggcaaggctg gcccggtcgg caccagttgc gtgagcggaa agatggccgc          950

ttcccggccc tgctgcaggg agctcaaaat ggaggacgcg gcgctcggga         1000

gagcgggcgg gtgagtcacc cacacaaagg aaaagggcct ttccgtcctc         1050

agccgtcgct tcatgtgact ccacggagta ccgggcgccg tccaggcacc         1100

tcgattagtt ctcgagcttt tggagtacgt cgtctttagg ttggggggag         1150

gggttttatg cgatggagtt tccccacact gagtgggtgg agactgaagt         1200

taggccagct tggcacttga tgtaattctc cttggaattt gccctttttg         1250

agtttggatc ttggttcatt ctcaagcctc agacagtggt tcaaagtttt         1300

tttcttccat ttcaggtgta cgcgtctcgg gaagctttag tttaaacgcc         1350

gtgagtggat ccatctggga taagcatgct gttttctgtc tgtccctaac         1400

atgccctgtg attatgcgca aacaacacac ccaagggcag aactttgtta         1450

cttaaacacc atcctgtttg cttctttcct cagga act gtg gct gca cca     1500
                                       Thr Val Ala Ala Pro
                                                         5

tct gtc ttc atc ttc ccg cca tct gat gag cag ttg aaa tct gga    1545
Ser Val Phe Ile Phe Pro Pro Ser Asp Glu Gln Leu Lys Ser Gly
                10                  15                  20

act gcc tct gtt gtg tgc ctg ctg aat aac ttc tat ccc aga gag    1590
Thr Ala Ser Val Val Cys Leu Leu Asn Asn Phe Tyr Pro Arg Glu
                25                  30                  35

gcc aaa gta cag tgg aag gtg gat aac gcc ctc caa tcg ggt aac    1635
Ala Lys Val Gln Trp Lys Val Asp Asn Ala Leu Gln Ser Gly Asn
                40                  45                  50

tcc cag gag agt gtc aca gag cag gac agc aag gac agc acc tac    1680
Ser Gln Glu Ser Val Thr Glu Gln Asp Ser Lys Asp Ser Thr Tyr
                55                  60                  65

agc ctc agc agc acc ctg acg ctg agc aaa gca gac tac gag aaa    1725
Ser Leu Ser Ser Thr Leu Thr Leu Ser Lys Ala Asp Tyr Glu Lys
                70                  75                  80

cac aaa gtc tac gcc tgc gaa gtc acc cat cag ggc ctg agc tcg    1770
His Lys Val Tyr Ala Cys Glu Val Thr His Gln Gly Leu Ser Ser
                85                  90                  95

ccc gtc aca aag agc ttc aac agg gga gag tgt tga                1806
Pro Val Thr Lys Ser Phe Asn Arg Gly Glu Cys
                100                 105

gctagaacta actaactaag ctagcaacgg tttccctcta gcgggatcaa         1856

ttccgccccc ccccctaac gttactggcc gaagccgctt ggaataaggc          1906

cggtgtgcgt ttgtctatat gttattttcc accatattgc cgtcttttgg         1956

caatgtgagg gcccggaaac ctggccctgt cttcttgacg agcattccta         2006

ggggtctttc ccctctcgcc aaaggaatgc aaggtctgtt gaatgtcgtg         2056

aaggaagcag ttcctctgga agcttcttga agacaaacaa cgtctgtagc         2106

gaccctttgc aggcagcgga accccccacc tggcgacagg tgcctctgcg         2156

gccaaaagcc acgtgtataa gatacacctg caaaggcggc acaaccccag         2206
```

-continued

```
tgccacgttg tgagttggat agttgtggaa agagtcaaat ggctctcctc      2256
aagcgtattc aacaaggggc tgaaggatgc ccagaaggta ccccattgta      2306
tgggatctga tctggggcct cggtgcacat gctttacgtg tgtttagtcg      2356
aggttaaaaa acgtctaggc cccccgaacc acggggacgt ggttttcctt      2406
tgaaaaacac gataatacca tggttgaaca agatggattg cacgcaggtt      2456
ctccggccgc ttgggtggag aggctattcg gctatgactg ggcacaacag      2506
acaatcggct gctctgatgc cgccgtgttc cggctgtcag cgcaggggcg      2556
cccggttctt tttgtcaaga ccgacctgtc cggtgccctg aatgaactgc      2606
aggacgaggc agcgcggcta tcgtggctgg ccacgacggg cgttccttgc      2656
gcagctgtgc tcgacgttgt cactgaagcg ggaagggact ggctgctatt      2706
gggcgaagtg ccggggcagg atctcctgtc atctcacctt gctcctgccg      2756
agaaagtatc catcatggct gatgcaatgc ggcggctgca tacgcttgat      2806
ccggctacct gcccattcga ccaccaagcg aaacatcgca tcgagcgagc      2856
acgtactcgg atggaagccg gtcttgtcga tcaggatgat ctggacgaag      2906
agcatcaggg gctcgcgcca gccgaactgt tcgccaggct caaggcgcgc      2956
atgcccgacg gcgaggatct cgtcgtgacc catggcgatg cctgcttgcc      3006
gaatatcatg gtggaaaatg gccgcttttc tggattcatc gactgtggcc      3056
ggctgggtgt ggcggaccgc tatcaggaca tagcgttggc tacccgtgat      3106
attgctgaag agcttggcgg cgaatgggct gaccgcttcc tcgtgcttta      3156
cggtatcgcc gctcccgatt cgcagcgcat cgccttctat cgccttcttg      3206
acgagttctt ctgagtcgat cgacctggcg taatagcgaa gaggcccgca      3256
ccgatcgccc ttcccaacag ttgcgcagcc tgaatggcga atgggacgcg      3306
ccctgtagcg gcgcattaag cgcggcgggt gtggtggtta cgcgcagcgt      3356
gaccgctaca cttgccagcg ccctagcgcc cgctcctttc gctttcttcc      3406
cttcctttct cgccacgttc gccggctttc cccgtcaagc tctaaatcgg      3456
gggctccctt tagggttccg atttagtgct ttacggcacc tcgaccccaa      3506
aaaacttgat tagggtgatg gttcacgtag tgggccatcg ccctgataga      3556
cggtttttcg ccctttgacgt tggagtccac gttctttaat agtggactct      3606
tgttccaaac tggaacaaca ctcaacccta tctcggtcta tttataaggg      3656
attttgccga tttcggccta ttggttaaaa aatgagctga tttaacaaaa      3706
tttaacgcga attttaacaa aatattaacg cttacaattt aggtggcact      3756
tttcggggaa atgtgcgcgg aacccctata tttgtttatt tttctaaata      3806
cattcaaata tgtatccgct catgagacaa taaccctgat aaatgcttca      3856
ataatattga aaaaggaaga gtatgagtat tcaacatttc cgtgtcgccc      3906
ttattccctt ttttgcggca ttttgcctta ctgtttttgc tcacccagaa      3956
acgctggtga aagtaaaaga tgctgaagat cagttgggtg cacgagtggg      4006
ttacatcgaa ctggatctca acagcggtaa gatccttgag agttttcgcc      4056
ccgaagaacg ttttccaatg atgagcactt ttaaagttct gctatgtggc      4106
gcggtattat cccgtattga cgccgggcaa gagcaactcg gtcgccgcat      4156
acactattct cagaatgact tggttgagta ctcaccagtc acagaaaagc      4206
```

```
atattacgga tggcatgaca gtaagagaat tatgcagtgc tgccataacc      4256

atgagtgata acactgcggc caacttactt ctgacaacga tcggaggacc      4306

gaaggagcta accgcttttt tgcacaacat gggggatcat gtaactcgcc      4356

ttgatcgttg ggaaccggag ctgaatgaag ccataccaaa cgacgagcgt      4406

gacaccacga tgcctgtagc aatggcaaca acgttgcgca aactattaac      4456

tggcgaacta cttactctag cttcccggca acaattaata gactggatgg      4506

aggcggataa agttgcagga ccacttctgc gctcggccct tccggctggc      4556

tggtttattg ctgataaatc tggagccggt gagcgtgggt ctcgcggtat      4606

cattgcagca ctggggccag atggtaagcc ctcccgtatc gtagttatct      4656

acacgacggg gagtcaggca actatggatg aacgaaatag acagatcgct      4706

gagataggtg cctcactgat taagcattgg taactgtcag accaagttta      4756

ctcatatata ctttagattg atttaaaact tcatttttaa tttaaaagga      4806

tctaggtgaa gatccttttt gataatctca tgaccaaaat cccttaacgt      4856

gagttttcgt tccactgagc gtcagacccc gtagaaaaga tcaaaggatg      4906

ttcttgagat cctttttttc tgcacgtaat ctgctgcttg caaacaaaaa      4956

accaccgcta ccagcggtgg tttgtttgcc ggatcaagag ctaccaactc      5006

tttttccgaa ggtaactggc ttcagcagag cgcagatacc aaatactgtc      5056

cttctagtgt agccgtagtt aggccaccac ttcaagaact ctgtagcacc      5106

gcctacatac ctcgctctgc taatcctgtt accagtggct gctgccagtg      5156

gcgataagtc gtgtcttacc gggttggact caagacgata gttaccggat      5206

aaggcgcagc ggtcgggctg aacggggggt tcgtgcacac agcccagctt      5256

ggagcgaacg acctacaccg aactgagata cctacagcgt gagctatgag      5306

aaagcgccac gcttcccgaa gggagaaagg cggacaggta tccggtaagc      5356

ggcagggtcg gaacaggaga gcgcacgagg gagcttccag ggggaaacgc      5406

ctggtatctt tatagtcctg tcgggtttcg ccacctctga cttgagcgtc      5456

gatttttgtg atgctcgtca ggggggcgga gcctatggaa aaacgccagc      5506

aacgcggcct ttttacggtt cctggccttt tgctggcctt ttgctcacat      5556

gttctttcct gcgttatccc ctgattctgt ggataaccgt attaccgcct      5606

ttgagtgagc tgataccgct cgccgcagcc gaacgaccga gcgcagcgag      5656

tcagtgagcg aggaagcgga agagcgccca atacgcaaac cgcctctccc      5706

cgcgcgttgg ccgattcatt aatgcaggta tcacgaggcc ctttcgtctt      5756

cac                                                         5759
```

<210> SEQ ID NO 49
<211> LENGTH: 6207
<212> TYPE: DNA
<213> ORGANISM: Artificial Sequence
<220> FEATURE:
<223> OTHER INFORMATION: Heavy chain expression vector pREN-DHFR.

<400> SEQUENCE: 49

```
ctcgagagcg ggcagtgagc gcaacgcaat taatgtgagt tagctcactc        50

attaggcacc ccaggcttta cactttatgc tcccggctcg tatgttgtgt       100

ggagattgtg agcggataac aatttcacac agaattcgtg aggctccggt       150
```

```
gcccgtcagt gggcagagcg cacatcgccc acagtccccg agaagttggg          200

gggaggggtc ggcaattgaa ccggtgccta gagaaggtgg cgcggggtaa          250

actgggaaag tgatgtcgtg tactggctcc gcctttttcc cgagggtggg          300

ggagaaccgt atataagtgc agtagtcgcc gtgaacgttc tttttcgcaa          350

cgggtttgcc gccagaacac aggtaagtgc cgtgtgtggt tcccgcgggc          400

ctggcctctt tacgggttat ggcccttgcg tgccttgaat tacttccacg          450

cccctggctg cagtacgtga ttcttgatcc cgagcttcgg gttggaagtg          500

ggtgggagag ttcgaggcct tgcgcttaag gagccccttc gcctcgtgct          550

tgagttgagg cctggcctgg gcgctggggc cgccgcgtgc gaatctggtg          600

gcaccttcgc gcctgtctcg ctgctttcga taagtctcta gccatttaaa          650

atttttgatg acctgctgcg acgctttttt tctggcaaga tagtcttgta          700

aatgcgggcc aagatctgca cactggtatt tcggtttttg gggccgcggg          750

cggcgacggg gcccgtgcgt cccagcgcac atgttcggcg aggcggggcc          800

tgcgagcgcg gccaccgaga atcggacggg ggtagtctca agctggccgg          850

cctgctctgg tgcctggcct cgcgccgccg tgtatcgccc cgccctgggc          900

ggcaaggctg gcccggtcgg caccagttgc gtgagcggaa agatggccgc          950

ttcccggccc tgctgcaggg agctcaaaat ggaggacgcg gcgctcggga         1000

gagcgggcgg gtgagtcacc cacacaaagg aaaagggcct ttccgtcctc         1050

agccgtcgct tcatgtgact ccacggagta ccgggcgccg tccaggcacc         1100

tcgattagtt ctcgagcttt tggagtacgt cgtctttagg ttggggggag         1150

gggttttatg cgatggagtt tccccacact gagtgggtgg agactgaagt         1200

taggccagct tggcacttga tgtaattctc cttggaattt gccctttttg         1250

agtttggatc ttggttcatt ctcaagcctc agacagtggt tcaaagtttt         1300

cttccatttc aggtgtacgc gtctcgggaa gctttagttt aaacgcctgg         1350

atcctctgcg cctgggccca gctctgtccc acaccgcggt cacatggcac         1400

cacctctctt gcagcc tcc acc aag ggc cca tcg gtc ttc ccc ctg      1446
                  Ser Thr Lys Gly Pro Ser Val Phe Pro Leu
                                  5                   10

gca ccc tcc tcc aag agc acc tct ggg ggc aca gcg gcc ctg ggc    1491
Ala Pro Ser Ser Lys Ser Thr Ser Gly Gly Thr Ala Ala Leu Gly
                15                  20                  25

tgc ctg gtc aag gac tac ttc ccc gaa ccg gtg acg gtg tcg tgg    1536
Cys Leu Val Lys Asp Tyr Phe Pro Glu Pro Val Thr Val Ser Trp
                30                  35                  40

aac tca ggc gcc ctg acc agc ggc gtg cac acc ttc ccg gct gtc    1581
Asn Ser Gly Ala Leu Thr Ser Gly Val His Thr Phe Pro Ala Val
                45                  50                  55

cta cag tcc tca gga ctc tac tcc ctc agc agc gtg gtg acc gtg    1626
Leu Gln Ser Ser Gly Leu Tyr Ser Leu Ser Ser Val Val Ser Val
                60                  65                  70

ccc tcc agc agc ttg ggc acc cag acc tac atc tgc aac gtg aat    1671
Pro Ser Ser Ser Leu Gly Thr Gln Thr Tyr Ile Cys Asn Val Asn
                75                  80                  85

cac aag ccc agc aac acc aag gtg gac aag aaa gtt gag ccc aaa    1716
His Lys Pro Ser Asn Thr Lys Val Asp Lys Lys Val Glu Pro Lys
                90                  95                  100

tct tgt gac aaa act cac aca tgc cca ccg tgc cca gca cct gaa    1761
Ser Cys Asp Lys Thr His Thr Cys Pro Pro Cys Pro Ala Pro Glu
```

-continued

```
                105                 110                 115

ctc ctg ggg gga ccg tca gtc ttc ctc ttc ccc cca aaa ccc aag          1806
Leu Leu Gly Gly Pro Ser Val Phe Leu Phe Pro Pro Lys Pro Lys
                120                 125                 130

gac acc ctc atg atc tcc cgg acc cct gag gtc aca tgc gtg gtg          1851
Asp Thr Leu Met Ile Ser Arg Thr Pro Glu Val Thr Cys Val Val
                135                 140                 145

gtg gac gtg agc cac gaa gac cct gag gtc aag ttc aac tgg tac          1896
Val Asp Val Ser His Glu Asp Pro Glu Val Lys Phe Asn Trp Tyr
                150                 155                 160

gtg gac ggc gtg gag gtg cat aac gcc aag aca aag ccg cgg gag          1941
Val Asp Gly Val Glu Val His Asn Ala Lys Thr Lys Pro Arg Glu
                165                 170                 175

gag cag tac aac agc acg tac cgg gtg gtc agc gtc ctc acc gtc          1986
Glu Gln Tyr Asn Ser Thr Tyr Arg Val Val Ser Val Leu Thr Val
                180                 185                 190

ctg cac cag gac tgg ctg aat ggc aag gag tac aag tgc aag gtc          2031
Leu His Gln Asp Trp Leu Asn Gly Lys Glu Tyr Lys Cys Lys Val
                195                 200                 205

tcc aac aaa gcc ctc cca gcc ccc atc gag aaa acc atc tcc aaa          2076
Ser Asn Lys Ala Leu Pro Ala Pro Ile Glu Lys Thr Ile Ser Lys
                210                 215                 220

gcc aaa ggg cag ccc cga gaa cca cag gtg tac acc ctg ccc cca          2121
Ala Lys Gly Gln Pro Arg Glu Pro Gln Val Tyr Thr Leu Pro Pro
                225                 230                 235

tcc cgg gag gag atg acc aag aac cag gtc agc ctg acc tgc ctg          2166
Ser Arg Glu Glu Met Thr Lys Asn Gln Val Ser Leu Thr Cys Leu
                240                 245                 250

gtc aaa ggc ttc tat ccc agc gac atc gcc gtg gag tgg gag agc          2211
Val Lys Gly Phe Tyr Pro Ser Asp Ile Ala Val Glu Trp Glu Ser
                255                 260                 265

aat ggg cag ccg gag aac aac tac aag acc acg cct ccc gtg ctg          2256
Asn Gly Gln Pro Glu Asn Asn Tyr Lys Thr Thr Pro Pro Val Leu
                270                 275                 280

gac tcc gac ggc tcc ttc ttc ctc tac agc aag ctc acc gtg gac          2301
Asp Ser Asp Gly Ser Phe Phe Leu Tyr Ser Lys Leu Thr Val Asp
                285                 290                 295

aag agc agg tgg cag cag ggg aac gtc ttc tca tgc tcc gtg atg          2346
Lys Ser Arg Trp Gln Gln Gly Asn Val Phe Ser Cys Ser Val Met
                300                 305                 310

cat gag gct ctg cac aac cac tac acg cag aag agc ctc tcc ctg          2391
His Glu Ala Leu His Asn His Tyr Thr Gln Lys Ser Leu Ser Leu
                315                 320                 325

tct ccg ggt aaa tga gctagaaact aactaagcta gcaacggttt                2436
Ser Pro Gly Lys

ccctctagcg ggatcaattc cgcccccccc ccctaacgtt actggccgaa                2486

gccgcttgga ataaggccgg tgtgcgtttg tctatatgtt attttccacc                2536

atattgccgt cttttggcaa tgtgagggcc cggaaacctg gccctgtctt                2586

cttgacgagc attcctaggg gtctttcccc tctcgccaaa ggaatgcaag                2636

gtctgttgaa tgtcgtgaag gaagcagttc ctctggaagc ttcttgaaga                2686

caaacaacgt ctgtagcgac cctttgcagg cagcggaacc ccccacctgg                2736

cgacaggtgc ctctgcggcc aaaagccacg tgtataagat acacctgcaa                2786

aggcggcaca accccagtgc cacgttgtga gttggatagt tgtggaaaga                2836

gtcaaatggc tctcctcaag cgtattcaac aaggggctga aggatgccca                2886

gaaggtaccc cattgtatgg gatctgatct ggggcctcgg tgcacatgct                2936
```

```
ttacgtgtgt ttagtcgagg ttaaaaaacg tctaggcccc ccgaaccacg        2986

gggacgtggt tttcctttga aaaacacgat aataccatgg ttcgaccatt        3036

gaactgcatc gtcgccgtgt cccaaaatat ggggattggc aagaacggag        3086

acctaccctg gcctccgctc aggaacgagt tcaagtactt ccaaagaatg        3136

accacaacct cttcagtgga aggtaaacag aatctggtga ttatgggtag        3186

gaaaacctgg ttctccattc ctgagaagaa tcgaccttta aaggacagaa        3236

ttaatggttc gatatagttc tcagtagaga actcaaagaa ccaccacgag        3286

gagctcattt tcttgccaaa agtttggatg atgccttaag acttattgaa        3336

caaccggaat tggcaagtaa agtagacatg gtttggatag tcggaggcag        3386

ttctgtttac caggaagcca tgaatcaacc aggccacctc agactctttg        3436

tgacaaggat catgcaggaa tttgaaagtg acacgttttt cccagaaatt        3486

gatttgggga aatataaact tctcccagaa tacccaggcg tcctctctga        3536

ggtccaggag gaaaaaggca tcaagtataa gtttgaagtc tacgagaaga        3586

aagactaaca ggaagatgct ttcaagttct ctgctcccct cctaaagcta        3636

tgcattttta taagaccatg ggacttttgc tggtcgatcg acctggcgta        3686

atagcgaaga ggcccgcacc gatcgccctt cccaacagtt gcgcagcctg        3736

aatggcgaat gggacgcgcc ctgtagcggc gcattaagcg cggcgggtgt        3786

ggtggttacg cgcagcgtga ccgctacact tgccagcgcc ctagcgcccg        3836

ctcctttcgc tttcttccct tcctttctcg ccacgttcgc cggctttccc        3886

cgtcaagctc taaatcgggg gctcccttta gggttccgat ttagtgcttt        3936

acggcacctc gaccccaaaa aacttgatta gggtgatggt tcacgtagtg        3986

ggccatcgcc ctgatagacg gtttttcgcc tttgacgttg gagtccacgt        4036

tctttaatag tggactcttg ttccaaactg gaacaacact caaccctatc        4086

tcggtctatt tataagggat tttgccgatt tcggcctatt ggttaaaaaa        4136

tgagctgatt taacaaaatt taacgcgaat tttaacaaaa tattaacgct        4186

tacaatttag gtggcacttt tcggggaaat gtgcgcggaa cccctatatt        4236

tgtttatttt tctaaataca ttcaaatatg tatccgctca tgagacaata        4286

accctgataa atgcttcaat aatattgaaa aaggaagagt atgagtattc        4336

aacatttccg tgtcgccctt attccctttt ttgcggcatt ttgccttact        4386

gtttttgctc acccagaaac gctggtgaaa gtaaaagatg ctgaagatca        4436

gttgggtgca cgagtgggtt acatcgaact ggatctcaac agcggtaaga        4486

tccttgagag ttttcgcccc gaagaacgtt ttccaatgat gagcactttt        4536

aaagttctgc tatgtggcgc ggtattatcc cgtattgacg ccgggcaaga        4586

gcaactcggt cgccgcatac actattctca gaatgacttg gttgagtact        4636

caccagtcac agaaaagcat attacggatg gcatgacagt aagagaatta        4686

tgcagtgctg ccataaccat gagtgataac actgcggcca acttacttct        4736

gacaacgatc ggaggaccga aggagctaac cgcttttttg cacaacatgg        4786

gggatcatgt aactcgcctt gatcgttggg aaccggagct gaatgaagcc        4836

ataccaaacg acgagcgtga caccacgatg cctgtagcaa tggcaacaac        4886

gttgcgcaaa ctattaactg gcgaactact tactctagct tcccggcaac        4936
```

aattaataga ctggatggag gcggataaag ttgcaggacc acttctgcgc 4986 tcggcccttc cggctggctg gtttattgct gataaatctg gagccggtga 5036 gcgtgggtct cgcggtatca ttgcagcact ggggccagat ggtaagccct 5086 cccgtatcgt agttatctac acgacgggga gtcaggcaac tatggatgaa 5136 cgaaatagac agatcgctga gataggtgcc tcactgatta agcattggta 5186 actgtcagac caagtttact catatatact ttagattgat ttaaaacttc 5236 atttttaatt taaaaggatc taggtgaaga tcctttttga taatctcatg 5286 accaaaatcc cttaacgtga gttttcgttc cactgagcgt cagaccccgt 5336 agaaaagatc aaaggatgtt cttgagatcc tttttttctg cacgtaatct 5386 gctgcttgca aacaaaaaac caccgctacc agcggtggtt tgtttgccgg 5436 atcaagagct accaactctt tttccgaagg taactggctt cagcagagcg 5486 cagataccaa atactgtcct tctagtgtag ccgtagttag gccaccactt 5536 caagaactct gtagcaccgc ctacatacct cgctctgcta atcctgttac 5586 cagtggctgc tgccagtggc gataagtcgt gtcttaccgg gttggactca 5636 agacgatagt taccggataa ggcgcagcgg tcgggctgaa cggggggttc 5686 gtgcacacag cccagcttgg agcgaacgac ctacaccgaa ctgagatacc 5736 tacagcgtga gctatgagaa agcgccacgc ttcccgaagg gagaaaggcg 5786 gacaggtatc cggtaagcgg cagggtcgga acaggagagc gcacgaggga 5836 gcttccaggg ggaaacgcct ggtatcttta tagtcctgtc gggtttcgcc 5886 acctctgact tgagcgtcga tttttgtgat gctcgtcagg ggggcggagc 5936 ctatggaaaa acgccagcaa cgcggccttt ttacggttcc tggccttttg 5986 ctggcctttt gctcacatgt tctttcctgc gttatcccct gattctgtgg 6036 ataaccgtat taccgccttt gagtgagctg ataccgctcg ccgcagccga 6086 acgaccgagc gcagcgagtc agtgagcgag gaagcggaag agcgcccaat 6136 acgcaaaccg cctctccccg cgcgttggcc gattcattaa tgcaggtatc 6186 acgaggccct ttcgtcttca c 6207

<210> SEQ ID NO 50
<211> LENGTH: 444
<212> TYPE: DNA
<213> ORGANISM: Mus musculus
<220> FEATURE:
<223> OTHER INFORMATION: murine G250 heavy chain variable region

<400> SEQUENCE: 50
gtttaaacgc cgccaccatg aacttcgggc tcagattgat ttccttgtc 50 ctggttttaa aaggtgtcct gtgtgacgtg aagctcgtgg agtctggggc 100
agccttagtg aagcttggag ggtccctgaa actctcctgt gcagcctctg 150
gattcacttt cagtaactat tacatgtctt gggttcgcca gactccagag 200
aagaggctgg agttggtcgc agccattaat agtgatggtg gtatcaccta 250
ctatctagac actgtgaagg gccgattcac catttcaaga gacaatgcca 300
agaacaccct gtacctgcaa atgagcagtc tgaagtctga ggacacagcc 350
ttgttttact gtgcaagaca ccgctcaggc tacttttcta tggactactg 400
gggtcaagga acctcagtca ccgtctcctc aggtgagtgg atcc 444

```
<210> SEQ ID NO 51
<211> LENGTH: 140
<212> TYPE: PRT
<213> ORGANISM: Mus musculus
<220> FEATURE:
<223> OTHER INFORMATION: amino acid sequence for murine G250 heavy chain
      variable region

<400> SEQUENCE: 51

Met Asn Phe Gly Leu Arg Leu Ile Phe Leu Val Leu Val Leu Lys Gly
                5                   10                  15

Val Leu Cys Asp Val Lys Leu Val Glu Ser Gly Ala Ala Leu Val Lys
            20                  25                  30

Leu Gly Gly Ser Leu Lys Leu Ser Cys Ala Ala Ser Gly Phe Thr Phe
        35                  40                  45

Ser Asn Tyr Tyr Met Ser Trp Val Arg Gln Thr Pro Glu Lys Arg Leu
    50                  55                  60

Glu Leu Val Ala Ala Ile Asn Ser Asp Gly Gly Ile Thr Tyr Tyr Leu
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Phe Tyr Cys Ala Arg His Arg Ser Gly Tyr Phe Ser Met Asp Tyr Trp
        115                 120                 125

Gly Gln Gly Thr Ser Val Thr Val Ser Ser Gly Glu
    130                 135                 140


<210> SEQ ID NO 52
<211> LENGTH: 423
<212> TYPE: DNA
<213> ORGANISM: Mus musculus
<220> FEATURE:
<223> OTHER INFORMATION: murine G250 light chain variable region

<400> SEQUENCE: 52

gtttaaacgc cgccaccatg ggcttcaaga tggagtttca tactcaggtc                50

tttgtattcg tgtttctctg gttgtctggt gttgatggag acattgtgat               100

gacccagtct caaagattca tgtccacaac agtaggagac agggtcagca               150

tcacctgcaa ggccagtcag aatgtggttt ctgctgttgc ctggtatcaa               200

cagaaaccag gacaatctcc taaactactg atttactcag catccaatcg               250

gtacactgga gtccctgatc gcttcacagg cagtggatct gggacagatt               300

tcactctcac cattagcaat atgcagtctg aagacctggc tgattttttc               350

tgtcaacaat atagcaacta tccgtggacg ttcggtggag gcaccaagct               400

ggaaatcaaa cgtgagtgga tcc                                            423


<210> SEQ ID NO 53
<211> LENGTH: 132
<212> TYPE: PRT
<213> ORGANISM: Mus musculus
<220> FEATURE:
<223> OTHER INFORMATION: amino acid sequence for murine G250 light chain
      variable region

<400> SEQUENCE: 53

Met Gly Phe Lys Met Glu Phe His Thr Gln Val Phe Val Phe Val Phe
                5                   10                  15
```

```
Leu Trp Leu Ser Gly Val Asp Gly Asp Ile Val Met Thr Gln Ser Gln
            20                  25                  30

Arg Phe Met Ser Thr Thr Val Gly Asp Arg Val Ser Ile Thr Cys Lys
        35                  40                  45

Ala Ser Gln Asn Val Val Ser Ala Val Ala Trp Tyr Gln Gln Lys Pro
    50                  55                  60

Gly Gln Ser Pro Lys Leu Leu Ile Tyr Ser Ala Ser Asn Arg Tyr Thr
65                  70                  75                  80

Gly Val Pro Asp Arg Phe Thr Gly Ser Gly Ser Gly Thr Asp Phe Thr
                85                  90                  95

Leu Thr Ile Ser Asn Met Gln Ser Glu Asp Leu Ala Asp Phe Phe Cys
            100                 105                 110

Gln Gln Tyr Ser Asn Tyr Pro Trp Thr Phe Gly Gly Gly Thr Lys Leu
        115                 120                 125

Glu Ile Lys Arg
    130
```

<210> SEQ ID NO 54
<211> LENGTH: 482
<212> TYPE: DNA
<213> ORGANISM: Homo sapiens
<220> FEATURE:
<223> OTHER INFORMATION: nucleotide sequence of a TNF fragment

<400> SEQUENCE: 54

```
ccatggtctc atcttctcga accccgagtg acaagcctgt agcccatgtt              50

gtagcaaacc ctcaagctga ggggcagctc cagtggctga accgccgggc             100

caatgccctc ctggccaatg gcgtggagct gagagataac cagctggtgg             150

tgccatcaga gggcctgtac ctcatctact cccaggtcct cttcaagggc             200

caaggctgcc cctccaccca tgtgctcctc acccacacca tcagccgcat             250

cgccgtctcc taccagacca aggtcaacct cctctctgcc atcaagagcc             300

cctgccagag ggagacccca gaggggggctg aggccaagcc ctggtatgag            350

cccatctatc tgggaggggt cttccagctg gagaagggtg accgactcag             400

cgctgagatc aatcggcccg actatctcga ctttgccgag tctgggcagg             450

tctactttgg gatcattgcc ctgtgatcta ga                                482
```

<210> SEQ ID NO 55
<211> LENGTH: 157
<212> TYPE: PRT
<213> ORGANISM: Homo sapiens
<220> FEATURE:
<223> OTHER INFORMATION: amino acid sequence of a TNF fragment

<400> SEQUENCE: 55

```
Met Val Ser Ser Ser Arg Thr Pro Ser Asp Lys Pro Val Ala His Val
                5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80
```

```
Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 56
<211> LENGTH: 6047
<212> TYPE: DNA
<213> ORGANISM: Artificial Sequence
<220> FEATURE:
<223> OTHER INFORMATION: Heavy chain expression vector pREN-DHFR-TNF.

<400> SEQUENCE: 56

```
ctcgagagcg ggcagtgagc gcaacgcaat taatgtgagt tagctcactc        50

attaggcacc ccaggcttta cactttatgc tcccggctcg tatgttgtgt       100

ggagattgtg agcggataac aatttcacac agaattcgtg aggctccggt       150

gcccgtcagt gggcagagcg cacatcgccc acagtccccg agaagttggg       200

gggaggggtc ggcaattgaa ccggtgccta gagaaggtgg cgcggggtaa       250

actgggaaag tgatgtcgtg tactggctcc gcctttttcc cgagggtggg       300

ggagaaccgt atataagtgc agtagtcgcc gtgaacgttc tttttcgcaa       350

cgggtttgcc gccagaacac aggtaagtgc cgtgtgtggt tcccgcgggc       400

ctggcctctt tacgggttat ggcccttgcg tgccttgaat tacttccacg       450

cccctggctg cagtacgtga ttcttgatcc cgagcttcgg gttggaagtg       500

ggtgggagag ttcgaggcct tgcgcttaag gagccccttc gcctcgtgct       550

tgagttgagg cctggcctgg gcgctggggc cgccgcgtgc gaatctggtg       600

gcaccttcgc gcctgtctcg ctgctttcga taagtctcta gccatttaaa       650

atttttgatg acctgctgcg acgctttttt tctggcaaga tagtcttgta       700

aatgcgggcc aagatctgca cactggtatt tcggtttttg gggccgcggg       750

cggcgacggg gcccgtgcgt cccagcgcac atgttcggcg aggcggggcc       800

tgcgagcgcg gccaccgaga atcggacggg ggtagtctca agctggccgg       850

cctgctctgg tgcctggcct cgcgccgccg tgtatcgccc cgccctgggc       900

ggcaaggctg gcccggtcgg caccagttgc gtgagcggaa agatggccgc       950

ttcccggccc tgctgcaggg agctcaaaat ggaggacgcg gcgctcggga      1000

gagcgggcgg gtgagtcacc cacacaaagg aaaagggcct ttccgtcctc      1050

agccgtcgct tcatgtgact ccacggagta ccgggcgccg tccaggcacc      1100

tcgattagtt ctcgagcttt tggagtacgt cgtctttagg ttggggggag      1150

gggttttatg cgatggagtt tccccacact gagtgggtgg agactgaagt      1200

taggccagct tggcacttga tgtaattctc cttggaattt gccctttttg      1250

agtttggatc ttggttcatt ctcaagcctc agacagtggt tcaaagtttt      1300

tttcttccat ttcaggtgta cgcgtctcgg gaagctttag tttaaacgcc      1350

ggatcctctg cgcctgggcc cagctctgtc ccacaccgcg gtcacatggc      1400
```

```
accacctctc ttgcagcc tcc acc aag ggc cca tcg gtc ttc ccc ctg         1448
                    Ser Thr Lys Gly Pro Ser Val Phe Pro Leu
                                    5                   10

gca ccc tcc tcc aag agc acc tct ggg ggc aca gcg gcc ctg ggc         1493
Ala Pro Ser Ser Lys Ser Thr Ser Gly Gly Thr Ala Ala Leu Gly
                15                  20                  25

tgc ctg gtc aag gac tac ttc ccc gaa ccg gtg acg gtg tcg tgg         1538
Cys Leu Val Lys Asp Tyr Phe Pro Glu Pro Val Thr Val Ser Trp
                30                  35                  40

aac tca ggc gcc ctg acc agc ggc gtg cac acc ttc ccg gct gtc         1583
Asn Ser Gly Ala Leu Thr Ser Gly Val His Thr Phe Pro Ala Val
                45                  50                  55

cta cag tcc tca gga ctc tac tcc ctc agc agc gtg gtg acc gtg         1628
Leu Gln Ser Ser Gly Leu Tyr Ser Leu Ser Ser Val Val Ser Val
                60                  65                  70

ccc tcc agc agc ttg ggc acc cag acc tac atc tgc aac gtg aat         1673
Pro Ser Ser Ser Leu Gly Thr Gln Thr Tyr Ile Cys Asn Val Asn
                75                  80                  85

cac aag ccc agc aac acc aag gtg gac aag aaa gtt gag ccc aaa         1718
His Lys Pro Ser Asn Thr Lys Val Asp Lys Lys Val Glu Pro Lys
                90                  95                  100

tct tgt gac aaa act cac aca tgc cca ccg tgc cca ggt gga ggt         1763
Ser Cys Asp Lys Thr His Thr Cys Pro Pro Cys Pro Gly Gly Gly
                105                 110                 115

gga tca cca atg gtc tca tct tct cga acc ccg agt gac aag cct         1808
Gly Ser Pro Met Val Ser Ser Ser Arg Thr Pro Ser Asp Lys Pro
                120                 125                 130

gta gcc cat gtt gta gca aac cct caa gct gag ggg cag ctc cag         1853
Val Ala His Val Val Ala Asn Pro Gln Ala Glu Gly Gln Leu Gln
                135                 140                 145

tgg ctg aac cgc cgg gcc aat gcc ctc ctg gcc aat ggc gtg gag         1898
Trp Leu Asn Arg Arg Ala Asn Ala Leu Leu Ala Asn Glu Val Glu
                150                 155                 160

ctg aga gat aac cag ctg gtg gtg cca tca gag ggc ctg tac ctc         1943
Leu Arg Asp Asn Gln Leu Val Val Pro Ser Glu Gly Leu Tyr Leu
                165                 170                 175

atc tac tcc cag gtc ctc ttc aag ggc caa ggc tgc ccc tcc acc         1988
Ile Tyr Ser Gln Val Leu Phe Lys Gly Gln Gly Cys Pro Ser Thr
                180                 185                 190

cat gtg ctc ctc acc cac acc atc agc cgc atc gcc gtc tcc tac         2033
His Val Leu Leu Thr His Thr Ile Ser Arg Ile Ala Val Ser Tyr
                195                 200                 205

cag acc aag gtc aac ctc ctc tct gcc atc aag agc ccc tgc cag         2078
Gln Thr Lys Val Asn Leu Leu Ser Ala Ile Lys Ser Pro Cys Gln
                210                 215                 220

agg gag acc cca gag ggg gct gag gcc aag ccc tgg tat gag ccc         2123
Arg Glu Thr Pro Glu Gly Ala Glu Ala Lys Pro Trp Tyr Glu Pro
                225                 230                 235

atc tat ctg gga ggg gtc ttc cag ctg gag aag ggt gac cga ctc         2168
Ile Tyr Leu Gly Gly Val Phe Gln Leu Glu Lys Gly Asp Arg Leu
                240                 245                 250

agc gct gag atc aat cgg ccc gac tat ctc gac ttt gcc gag tct         2213
Ser Ala Glu Ile Asn Arg Pro Asp Tyr Leu Asp Phe Ala Glu Ser
                255                 260                 265

ggg cag gtc tac ttt ggg atc att gcc ctg tga tctagaaact              2256
Gly Gln Val Tyr Phe Gly Ile Ile Ala Leu
                270                 275

aactaagcta gcaacggttt ccctctagcg ggatcaattc cgcccccccc              2306

ccctaacgtt actggccgaa gccgcttgga ataaggccgg tgtgcgtttg              2356
```

```
tctatatgtt attttccacc atattgccgt cttttggcaa tgtgagggcc      2406
cggaaacctg gccctgtctt cttgacgagc attcctaggg gtctttcccc      2456
tctcgccaaa ggaatgcaag gtctgttgaa tgtcgtgaag gaagcagttc      2506
ctctggaagc ttcttgaaga caaacaacgt ctgtagcgac cctttgcagg      2556
cagcggaacc ccccacctgg cgacaggtgc ctctgcggcc aaaagccacg      2606
tgtataagat acacctgcaa aggcggcaca accccagtgc cacgttgtga      2656
gttggatagt tgtggaaaga gtcaaatggc tctcctcaag cgtattcaac      2706
aaggggctga aggatgccca gaaggtaccc cattgtatgg gatctgatct      2756
ggggcctcgg tgcacatgct ttacgtgtgt ttagtcgagg ttaaaaaacg      2806
tctaggcccc ccgaaccacg gggacgtggt tttcctttga aaaacacgat      2856
aataccatgg ttcgaccatt gaactgcatc gtcgccgtgt cccaaaatat      2906
ggggattggc aagaacggag acctaccctg gcctccgctc aggaacgagt      2956
tcaagtactt ccaaagaatg accacaacct cttcagtgga aggtaaacag      3006
aatctggtga ttatgggtag gaaaacctgg ttctccattc ctgagaagaa      3056
tcgaccttta aaggacagaa ttaatggttc gatatagttc tcagtagaga      3106
actcaaagaa ccaccacgag gagctcattt tcttgccaaa agtttggatg      3156
atgccttaag acttattgaa caaccggaat tggcaagtaa agtagacatg      3206
gtttggatag tcggaggcag ttctgtttac caggaagcca tgaatcaacc      3256
aggccacctc agactctttg tgacaaggat catgcaggaa tttgaaagtg      3306
acacgttttt cccagaaatt gatttgggga aatataaact tctcccagaa      3356
tacccaggcg tcctctctga ggtccaggag gaaaaaggca tcaagtataa      3406
gtttgaagtc tacgagaaga aagactaaca ggaagatgct ttcaagttct      3456
ctgctcccct cctaaagcta tgcattttta taagaccatg ggacttttgc      3506
tggtcgatcg acctggcgta atagcgaaga ggcccgcacc gatcgccctt      3556
cccaacagtt gcgcagcctg aatggcgaat gggacgcgcc ctgtagcggc      3606
gcattaagcg cggcgggtgt ggtggttacg cgcagcgtga ccgctacact      3656
tgccagcgcc ctagcgcccg ctcctttcgc tttcttccct tcctttctcg      3706
ccacgttcgc cggctttccc cgtcaagctc taaatcgggg gctcccttta      3756
gggttccgat ttagtgcttt acggcacctc gaccccaaaa aacttgatta      3806
gggtgatggt tcacgtagtg ggccatcgcc ctgatagacg gtttttcgcc      3856
tttgacgttg gagtccacgt tctttaatag tggactcttg ttccaaactg      3906
gaacaacact caaccctatc tcggtctatt tataagggat tttgccgatt      3956
tcggcctatt ggttaaaaaa tgagctgatt taacaaaatt taacgcgaat      4006
tttaacaaaa tattaacgct tacaatttag gtggcacttt tcggggaaat      4056
gtgcgcggaa cccctatatt tgtttatttt tctaaataca ttcaaatatg      4106
tatccgctca tgagacaata accctgataa atgcttcaat aatattgaaa      4156
aaggaagagt atgagtattc aacatttccg tgtcgccctt attccctttt      4206
ttgcggcatt ttgccttact gtttttgctc acccagaaac gctggtgaaa      4256
gtaaaagatg ctgaagatca gttgggtgca cgagtgggtt acatcgaact      4306
ggatctcaac agcggtaaga tccttgagag ttttcgcccc gaagaacgtt      4356
```

-continued

```
ttccaatgat gagcactttt aaagttctgc tatgtggcgc ggtattatcc          4406

cgtattgacg ccgggcaaga gcaactcggt cgccgcatac actattctca          4456

gaatgacttg gttgagtact caccagtcac agaaaagcat attacggatg          4506

gcatgacagt aagagaatta tgcagtgctg ccataaccat gagtgataac          4556

actgcggcca acttacttct gacaacgatc ggaggaccga aggagctaac          4606

cgcttttttg cacaacatgg gggatcatgt aactcgcctt gatcgttggg          4656

aaccggagct gaatgaagcc ataccaaacg acgagcgtga caccacgatg          4706

cctgtagcaa tggcaacaac gttgcgcaaa ctattaactg gcgaactact          4756

tactctagct tcccggcaac aattaataga ctggatggag gcggataaag          4806

ttgcaggacc acttctgcgc tcggcccttc cggctggctg gtttattgct          4856

gataaatctg gagccggtga gcgtgggtct cgcggtatca ttgcagcact          4906

ggggccagat ggtaagccct cccgtatcgt agttatctac acgacgggga          4956

gtcaggcaac tatggatgaa cgaaatagac agatcgctga gataggtgcc          5006

tcactgatta agcattggta actgtcagac caagtttact catatatact          5056

ttagattgat ttaaaacttc atttttaatt taaaaggatc taggtgaaga          5106

tcctttttga taatctcatg accaaaatcc cttaacgtga gttttcgttc          5156

cactgagcgt cagaccccgt agaaaagatc aaaggatgtt cttgagatcc          5206

tttttttctg cacgtaatct gctgcttgca aacaaaaaac caccgctacc          5256

agcggtggtt tgtttgccgg atcaagagct accaactctt tttccgaagg          5306

taactggctt cagcagagcg cagataccaa atactgtcct tctagtgtag          5356

ccgtagttag gccaccactt caagaactct gtagcaccgc ctacatacct          5406

cgctctgcta atcctgttac cagtggctgc tgccagtggc gataagtcgt          5456

gtcttaccgg gttggactca agacgatagt taccggataa ggcgcagcgg          5506

tcgggctgaa cggggggttc gtgcacacag cccagcttgg agcgaacgac          5556

ctacaccgaa ctgagatacc tacagcgtga gctatgagaa agcgccacgc          5606

ttcccgaagg gagaaaggcg gacaggtatc cggtaagcgg cagggtcgga          5656

acaggagagc gcacgaggga gcttccaggg ggaaacgcct ggtatcttta          5706

tagtcctgtc gggtttcgcc acctctgact tgagcgtcga tttttgtgat          5756

gctcgtcagg ggggcggagc ctatggaaaa acgccagcaa cgcggccttt          5806

ttacggttcc tggccttttg ctggcctttt gctcacatgt tctttcctgc          5856

gttatcccct gattctgtgg ataaccgtat taccgccttt gagtgagctg          5906

ataccgctcg ccgcagccga acgaccgagc gcagcgagtc agtgagcgag          5956

gaagcggaag agcgcccaat acgcaaaccg cctctccccg cgcgttggcc          6006

gattcattaa tgcaggtatc acgaggccct ttcgtcttca c                   6047
```

HUMANIZED GM-CSF ANTIBODIES

RELATED APPLICATION

This application is a divisional of application Ser. No. 10/365,123, filed Feb. 12, 2003, now U.S. No. 7,381,801 which claims priority of application Ser. No. 60/355,838, filed Feb. 13, 2002, and incorporated by reference in their entirety.

FIELD OF THE INVENTION

This invention relates to the field of molecular immunology, generally, and to vectors useful for expression of proteins, especially antibodies, such as fully human, humanized, and chimeric antibodies, as well as fusion proteins which incorporate the antibody and a protein or protein fragment, in eukaryotic cells, mammalian cells in particular. The resulting antibodies and fusion proteins are also a feature of the invention.

BACKGROUND AND PRIOR ART

One serious problem with using murine antibodies for therapeutic applications in humans is that they quickly raise a human anti-mouse response (HAMA) which reduces the efficacy of the antibody in patients, and prevents continued administration thereof. Parallel issues arise with the administration of antibodies from other, non-human species. One approach to overcoming this problem is to generate so-called "chimeric" antibodies. These can comprise murine variable regions, and human constant regions (Boulianne et al. (1984) *Nature* 312(5995): 643-646.; incorporated by reference herein in its entirety). Although chimeric antibodies contain murine sequences and can elicit an anti-mouse response in humans (LoBuglio et al. (1989) *Proc. Natl. Acad. Sci. USA* 86(11): 4220-4224; incorporated by reference herein in its entirety), trials with chimeric antibodies in the area of hematological disease (e.g., Non-Hodgkin-Lymphoma; Witzig et al. (1999) *J. Clin. Oncol.* 17(12): 3793-3803; incorporated by reference herein in its entirety) or autoimmune disease (e.g., rheumatoid arthritis, chronic inflammatory bowel disease; Van den Bosch; et al, Lancet 356(9244):1821-2 (2000), incorporated by reference herein in its entirety) have led to FDA approval and demonstrate that these molecules have significant clinical potential and efficacy.

Recent studies have indicated that granulocyte-macrophage colony stimulating growth factor (GM-CSF) plays a role in the development of rheumatoid arthritis (RA) (Cook, et al., Arthritis Res. 2001, 3:293-298, incorporated by reference herein in its entirety) and possibly other inflammatory diseases and conditions. Therefore, it would be of interest to develop a drug which would block GM-CSF and its effect on cells. The present invention provides a chimeric antibody, targeting the GM-CSF molecule, which has blocking capacity.

The increased use of chimeric antibodies in therapeutic applications has created the need for expression vectors that effectively and efficiently produce high yields of functional chimeric antibodies in eukaryotic cells, such as mammalian cells, which are preferred for production. The present invention provides novel expression vectors, transformed host cells and methods for producing chimeric antibodies in mammalian cells, as well as the antibodies themselves and fusion proteins containing them.

SUMMARY OF INVENTION

Figure 1:
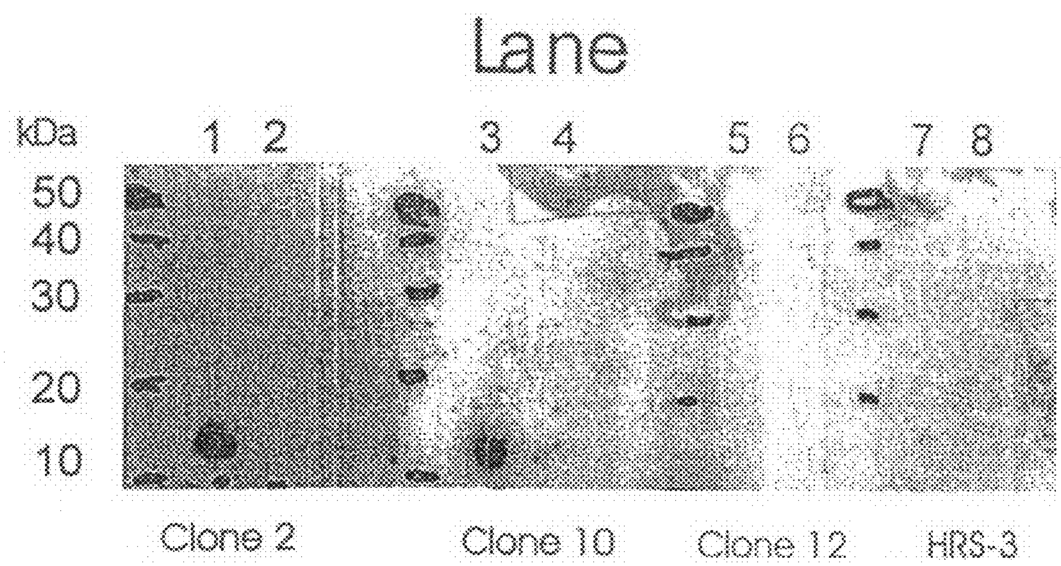
FIG. 1 shows the binding of recombinant, chimeric anti GM-CSF antibody via Western Blotting.

The present invention provides expression vectors which are useful in the expression of proteins, such as antibodies, especially fully human, humanized or chimerized antibodies, and fusion proteins containing these. Both light chains and heavy chains can be expressed. The expression vectors of the present invention comprise a human elongation factor 1 $\alpha$ (EF1$\alpha$) promoter/enhancer sequence, an internal ribosome entry site (IRES) sequence (U.S. Pat. No. 4,937,190; incorporated herein in its entirety), a nucleotide sequence that confers neomycin resistance to a cell containing the expression vector, and a nucleotide sequence under control of a simian virus 40 promoter (SV40) that confers ampicillin resistance to a cell containing the expression vector. In a preferred embodiment, the EF1$\alpha$ promoter/enhancer sequence is upstream and adjacent to a nucleotide sequence encoding a chimeric light chain.

The expression vector of the present invention may contain a nucleotide sequence encoding any immunoglobulin light chain. In a preferred embodiment the light chain variable region is of murine origin, and the light chain constant region is either human kappa or human lambda. In a more preferred embodiment, the chimeric light chain variable region is derived from a murine antibody that binds to GM-CSF, CD-30, or G250 and in especially preferred embodiments, to the human forms of these molecules.

The present invention also provides a further expression vector useful in the expression of proteins, such as antibodies, especially fully human, humanized or chimeric antibodies, and fusion proteins containing these. This second embodiment differs from the first in that instead of the neomycin resistance sequence, described supra, it comprises a nucleotide sequence which encodes dihydrofolate reductase or "dhfr," which generates resistance against the well known selection marker methotrexate. Such an expression vector may contain nucleotide sequences encoding any antibody or portion thereof, such as heavy or light chains of fully human, humanized or chimerized antibodies. In a preferred embodiment, a heavy chain is expressed, where the variable region is of murine origin, and the heavy chain constant region is human IgG1. In a more preferred embodiment, the chimeric heavy chain variable region is derived from a murine antibody that binds CD-30, GM-CSF or G250, preferably the human forms of these.

In another embodiment, the present invention provides host cells transformed or transfected with any one of the expression vectors of the present invention. In a preferred embodiment, a host cell, preferably a eukaryotic cell, more preferably a mammalian cell, is transformed or transfected with an expression vector comprising a chimeric immunoglobulin light chain and an expression vector comprising a chimeric immunoglobulin heavy chain. The present invention contemplates prokaryotic and eukaryotic cells, such as mammalian cells, insect cells, bacterial or fungal cells. In a preferred embodiment, the host cell is a human or Chinese Hamster Ovary ("CHO") cell.

The present invention also provides methods for the recombinant production of a chimeric immunoglobulin light or heavy chain comprising the step of culturing a transformed or transfected host cell of the present invention. In one embodiment, the methods of the present invention further comprise the isolation of the chimeric immunoglobulin light or heavy chain.

The present invention also provides methods for the recombinant production of a fully human, humanized or chimeric immunoglobulin comprising culturing a host cell that has been transformed or transfected with an expression vector comprising a chimeric immunoglobulin light chain and an expression vector comprising a chimeric immunoglobulin heavy chain, or an expression vector encodes both chains. In one embodiment, the methods of the present invention further comprise the self-assembly of the chimeric heavy and light chain immunoglobulins and isolation of the chimeric immunoglobulin. Methods for accomplishing this are well known in the art.

The present invention also provides the chimeric immunoglobulin light chain, heavy chain or assembled chimeric immunoglobulin produced by the methods of the present invention. In another embodiment, the present invention provides compositions comprising the chimeric immunoglobulin light chain, heavy chain or assembled chimeric immunoglobulin of the present invention and a pharmaceutically acceptable carrier.

DETAILED DESCRIPTION OF INVENTION

1. Definitions

As used herein "chimerized" refers to an immunoglobulin such as an antibody, wherein the heavy and light chains of the variable regions are not of human origin and wherein the constant regions of the heavy and light chains are of human origin.

"Humanized" refers to an immunoglobulin such as an antibody, wherein the amino acids directly involved in antigen binding, the so-called complementary determining regions (CDR), of the heavy and light chains are not of human origin, while the rest of the immunoglobulin molecule, the so-called framework regions of the variable heavy and light chains, and the constant regions of the heavy and light chains are of human origin.

"Fully human" refers to an immunoglobulin, such as an antibody, where the whole molecule is of human origin or consists of an amino acid sequence identical to a human form of the antibody.

"Immunoglobulin" or "antibody" refers to any member of a group of glycoproteins occurring in higher mammals that are major components of the immune system. As used herein, "immunoglobulins" and "antibodies" comprise four polypeptide chains—two identical light chains and two identical heavy chains that are linked together by disulfide bonds. An immunoglobulin molecule includes antigen binding domains, which each include the light chains and the end-terminal portion of the heavy chain, and the $F_c$ region, which is necessary for a variety of functions, such as complement fixation. There are five classes of immunoglobulins wherein the primary structure of the heavy chain, in the $F_c$ region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure.

"Antigen-binding fragment", "antigen-binding domain" and "Fab fragment" all refer to the about 45 kDa fragment obtained by papain digestion of an immunoglobulin molecule and consists of one intact light chain linked by a disulfide bond to the N-terminal portion of the contiguous heavy chain. As used herein, "$F(ab)_2$ fragment" refers to the about 90 kDa protein produced by pepsin hydrolysis of an immunoglobulin molecule. It consists of the N-terminal pepsin cleavage product and contains both antigen binding fragments of a divalent immunoglobulin, such as IgD, IgE, and IgG. Neither the "antigen-binding fragment" nor "$F(ab)_2$ fragment" contain the about 50 kDa $F_c$ fragment produced by papain digestion of an immunoglobulin molecule that contains the C-terminal halves of the immunoglobulin heavy chains, which are linked by two disulfide bonds, and contain sites necessary for compliment fixation.

"Epitope" refers to an immunological determinant of an antigen that serves as an antibody-binding site. Epitopes can be structural or conformational.

"Hybridoma" refers to the product of a cell-fusion between a cultured neoplastic lymphocyte and a normal, primed B- or T-lymphocyte, which expresses the specific immune potential of the parent cell.

"Heavy chain" refers to the longer & heavier of the two types of polypeptide chain in immunoglobulin molecules that contain the antigenic determinants that differentiate the various Ig classes, e.g., IgA, IgD, IgE, IgG, IgM, and the domains necessary for complement fixation, placental transfer, mucosal secretion, and interaction with $F_c$ receptors.

"Light chain" refers to the shorter & lighter of the two types of polypeptide chain in an Ig molecule of any class. Light chains, like heavy chains, comprise variable and constant regions.

"Heavy chain variable region" refers to the amino-terminal domain of the heavy chain that is involved in antigen binding and combines with the light chain variable region to form the antigen-binding domain of the immunoglobulin.

"Heavy chain constant region" refers to one of the three heavy chain domains that are carboxy-terminal portions of the heavy chain.

"Light chain variable region" refers to the amino-terminal domain of the light chain and is involved in antigen binding and combines with the heavy chain to form the antigen-binding region.

"Light chain constant region" refers to the one constant domain of each light chain. The light chain constant region consists of either kappa or lambda chains.

"Murine anti-human-GM-CSF 19/2 antibody" refers to a murine monoclonal antibody that is specific for human GM-CSF. This antibody is well known and it has been studied in detail. See Dempsey, et al, Hybridoma 9:545-58 (1990); Nice, et al, Growth Factors 3:159-169 (1990), both incorporated by reference.

"Effective amount" refers to an amount necessary to produce a desired effect.

"Antibody" refers to any glycoprotein of the immunoglobulin family that non-covalently, specifically, and reversibly binds a corresponding antigen.

"Monoclonal antibody" refers to an immunoglobulin produced by a single clone of antibody-producing cells. Unlike polyclonal antiserum, monoclonal antibodies are monospecific (e.g., specific for a single epitope of a single antigen).

"Granulocytes" include neutrophils, eosinophils, and basophils.

"GM-CSF" refers to a family of glycoprotein growth factors that control the production, differentiation, and function of granulocytes and monocytes-macrophages. Exemplary, but by no means the only form of such molecules, can be seen in U.S. Pat. No. 5,602,007, incorporated by reference.

"Inflammatory condition" refers to immune reactions that are either specific or non-specific. For example, a specific reaction is an immune reaction to an antigen. Examples of specific reactions include antibody responses to antigens, such as viruses and allergens, including delayed-type hypersensitivity, including psoriasis, asthma, delayed type hypersensitivity, inflammatory bowel disease, multiple sclerosis, viral pneumonia, bacterial pneumonia, and the like. A non-specific reaction is an inflammatory response that is mediated by leukocytes such as macrophages, eosinophils and neutrophils. Examples of non-specific reactions include the immediate swelling after a bee sting, and the collection of polymorphonuclear (PMN) leukocytes at sites of bacterial infection. Other "inflammatory conditions" within the scope of this invention include, e.g., autoimmune disorders such as psoriasis, rheumatoid arthritis, lupus, post-ischemic leukocyte mediated tissue damage (reperfusion injury), frost-bite injury or shock, acute leukocyte-mediated lung injury (acute respiratory distress syndrome or ARDS), asthma, traumatic shock, septic shock, nephritis, acute and chronic inflammation, and platelet-mediated pathologies such as ateriosclerosis and inappropriate blood clotting.

"Pharmaceutically acceptable carrier" refers to any carrier, solvent, diluent, vehicle, excipient, adjuvant, additive, preservative, and the like, including any combination thereof, that is routinely used in the art.

Physiological saline solution, for example, is a preferred carrier, but other pharmaceutically acceptable carriers are also contemplated by the present invention. The primary solvent in such a carrier may be either aqueous or non-aqueous. The carrier may contain other pharmaceutically acceptable excipients for modifying or maintaining pH, osmolarity, viscosity, clarity, color, sterility, stability, rate of dissolution, and/or odor. Similarly, the carrier may contain still other pharmaceutically acceptable excipients for modifying or maintaining the stability, rate of dissolution, release, or absorption or penetration across the blood-brain barrier.

The fully human, humanized or chimerized antibodies of the present invention may be administered orally, topically, parenterally, rectally or by inhalation spray in dosage unit formulations that contain conventional non-toxic pharmaceutically acceptable carriers, adjuvants and vehicles. As used herein, "parenterally" refers to subcutaneous, intravenous, intramuscular, intrasternal, intrathecal, and intracerebral injection, including infusion techniques.

The fully human, humanized or chimerized antibodies may be administered parenterally in a sterile medium. The antibodies, depending on the vehicle and concentration used, may be suspended or dissolved in the vehicle. Advantageously, adjuvants such as local anesthetics, preservatives and buffering agents can be dissolved in the vehicle. The most preferred routes of administration of the pharmaceutical compositions of the invention are subcutaneous, intramuscular, intrathecal or intracerebral administration. Other embodiments of the present invention encompass administration of the composition in combination with one or more agents that are usually and customarily used to formulate dosages for parenteral administration in either unit dose or multi-dose form, or for direct infusion.

Active ingredient may be combined with the carrier materials in amounts necessary to produce single dosage forms. The amount of the active ingredient will vary, depending upon the type of antibody used, the host treated, the particular mode of administration, and the condition from which the subject suffers. Preferably, the amount of fully human, humanized or chimerized anti-GM-CSF immunoglobulin, for example, is a therapeutically effective amount which is sufficient to decrease an inflammatory response or ameliorate the symptoms of an inflammatory condition. It will be understood by those skilled in the art, however, that specific dosage levels for specific patients will depend upon a variety of factors, including the activity of the specific immunoglobulins utilized, the age, body weight, general health, sex, diet, time of administration, route of administration, and rate of excretion, drug combination and the severity of the particular disease undergoing therapy. Administration of the fully human, humanized or chimerized immunoglobulins of the present invention may require either one or multiple dosings.

Regardless of the manner of administration, however, the specific dose is calculated according to approximate body weight or body surface area of the patient. Further refinement of the dosing calculations necessary to optimize dosing for each of the contemplated formulations is routinely conducted by those of ordinary skill in the art without undue experimentation, especially in view of the dosage information and assays disclosed herein.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Cloning Strategy for 19/2 Heavy (H) and Light (L) Variable (V)-Region Genes Total RNA from the hybridoma producing murine 19/2 antibody was obtained by standard RNA isolation techniques (Chomczynski et al. (1987) *Anal. Biochem.* 162: 156-159; incorporated by reference herein in its entirety). First strand cDNA was prepared using a commercially available, first strand cDNA synthesis kit and priming with d(T)18 for both the heavy and light chains (Renner et al. (1998) *Biotechniques* 24(5): 720-722; incorporated by reference herein in its entirety). The resulting cDNA was subjected to PCR using combinations of primers for the heavy and light chains. The nucleotide sequences of the 5' primers for the heavy and light chains are shown in Tables 1 and 2 respectively. The 3' primers are shown in Table 3. The light chain primer hybridized within the mouse kappa constant region not far from the V-C junction. The heavy chain 3' primer hybridised within the CH-1 constant region of mouse heavy chain subgroup 1 not far from the V-CH1 junction.

TABLE 1

Oligonucleotide primers for the 5' region of Mouse Heavy Variable (MHV) domains.

| | | SEQ ID NO: 1 |
|---|---|---|
| MHV-1: | 5'ATGAAATGCAGCTGGGTCATSTTCTTC 3' | 1 |
| MHV-2: | 5'ATGGGATGGAGCTRATCATSYTCTT 3' | 2 |
| MHV-3: | 5'ATGAAGWTGTGGTTAAACTGGGTTTTT 3' | 3 |
| MHV-4: | 5'ATGRACTTTGWYTCAGCTTGRTTT 3' | 4 |
| MHV-5: | 5'ATGGACTCCAGGCTCAAMAGTTTTCCTT 3' | 5 |
| MHV-6: | 5'ATGGCTGTCYTRGSGCTRCTCTTCTGC 3' | 6 |
| MHV-7: | 5'ATGGRATGGAGCKGGRTCTTTMTCTT 3' | 7 |
| MHV-8: | 5'ATGAGAGTGCTGATTCTTTTGTG 3' | 8 |
| MHV-9: | 5'ATGGMTTGGGTGTGGAMCTTGCTATTCCTG 3' | 9 |
| MHV-10: | 5'ATGGGCAGACTTACATTCTCATTCCTG 3' | 10 |
| MHV-11: | 5'ATGGATTTTGGGCTGATTTTTTTTATTG 3' | 11 |
| MHV-12: | 5'ATGATGGTGTTAAGTCTTCTGTACCTG 3' | 12 |

NB KEY R = A/G, Y = T/C, W = A/T, K = T/G, M = A/C, S = C/G.

TABLE 2

Oligonucleotides primers for the 5' region of Mouse Kappa Variable (MKV) domains.

| | | SEQ ID NO: 1 |
|---|---|---|
| MKV-1: | 5'ATGAAGTTGCCTGTTAGGCTGTTGGTGCTG 3' | 13 |
| MKV-2: | 5'ATGGAGWCAGACACACTCCTGYTATGGGT 3' | 14 |
| MKV-3: | 5'ATGAGTGTGCTCACTCAGGTCCTGGSGTTG 3' | 15 |
| MKV-4: | 5'ATGAGGRCCCCTGCTCAGWTTYTTGGMWTCTT G 3' | 16 |
| MKV-5: | 5'ATGGATTTWCAGGTGCAGATTWTCAGCTTC 3' | 17 |
| MKV-6: | 5'ATGAGGTKCYYTGYTSAGYTYCTGRGG 3' | 18 |
| MKV-7: | 5'ATGGGCWTCAAGATGGAGTCACAKWYYCWGG 3' | 19 |
| MKV-8: | 5'ATGTGGGGAYCTKTTTYCMMTTTTTCAATTG 3' | 20 |
| MKV-9: | 5'ATGGTRTCCWCASCTCAGTTCCTTG 3' | 21 |
| MKV-10: | 5'ATGTATATATGTTTGTTGTCTATTTCT 3' | 22 |
| MKV-11: | 5'ATGGAAGCCCCAGCTCAGCTTCTCTTCC 3' | 23 |
| MKV-12: | 5'ATGAAGTTTCCTTCTCAACTTCTGCTC 3' | 24 |

NB KEY R = A/G, Y = T/C, W = A/T, K = T/G, M = A/C, S = C/G.

TABLE 3

Oligonucleotide primers for the 3' ends of mouse VH and VL genes.

| | | |
|---|---|---|
| Light chain (MKC): | 5'TGGATGGTGGGAAGATG 3' | 25 |
| Heavy chain (MHC): | 5'CCAGTGGATAGACAGATG 3' | 26 |

Example 2

Ig Sequences Cloned from the 19/2 Murine Hybridoma

Using the cloning strategy described, supra, PCR products for VH and VL of murine 19/2 were cloned using a commercially available product, and art recognized techniques. For the murine 19/2 VL region, PCR products were obtained using the mouse kappa constant region primer and primers MKV2 and MKV7 (SEQ ID NOS: 14 & 19). For the mouse 19/2 VH region, PCR products were obtained using the mouse gamma 1 constant region primer and primers MHV2, MHV5 and MHV7 (SEQ ID NOS: 2, 5 and 7). Extensive DNA sequencing of the cloned V-region inserts revealed two different light chain sequences and 2 different heavy chain sequences. Pseudogenes for heavy and light chain were amplified and were eliminated by standard sequence analyses. A novel immunoglobulin-coding sequence was determined for both the heavy and light chains. This is set forth at SEQ ID NOS: 27, 28, 29 & 30, which present the cDNA and amino acid sequences for the murine 19/2 heavy chain variable region (27 & 28), and the light chain variable region (29 & 30).

Example 3

Mouse 19/2 Heavy Chain Leader Sequence

When comparing the DNA sequence of the leader sequence for 19/2 heavy chain obtained with the primers described supra, with the database, it appeared that the 19/2 HC leader sequence is short (17 amino acids) and unique vis a vis public data bases. Specifically, amino acids 2, 3 and 5 were E, L & M, as compared to S, W & F in the data bases. As compared to the database, hydrophilic amino acids in the N-terminal region were separated by neutral or basic ones, respectively; however, since the influence of these changes on the secretory capability of the leader sequence is unclear, this sequence was unaltered in further experiments.

Example 4

Construction of Mouse-Human Chimeric Genes

The chimeric 19/2 antibody was designed to have the mouse 19/2 VL and VH regions linked to human kappa and gamma-1 constant regions, respectively. PCR primers were used to modify the 5'- and 3'-sequences flanking the cDNA sequences coding for the mouse 19/2 VL and VH regions. PCR primers specific for 19/2 light chain V-region were designed using the sequence of the 19/2 light chain V-region gene obtained. These adapted mouse 19/2 variable regions were then subcloned into mammalian cell expression vectors already containing the human kappa (pREN-Neo vector) or the gamma-1 (pREN-DHFR vector) constant regions. The vectors employ parts of the human elongation factor 1α (EF1α) promoter/enhancer sequence to efficiently transcribe the light and heavy chains. The vectors also contain an IRES sequence following the multiple cloning site to allow for stringent, bicistronic expression and control of the individual selection marker in CHO cells. This pair of vectors was used in all of the recombinant work described herein, i.e., to manufacture all chimeric antibodies. The expression vectors were designed to have the variable regions inserted as PmeI-BamHI DNA fragments. PCR primers were designed to introduce these restrictions sites at the 5'- (PmeI) and 3'- (BamHI)

ends of the cDNAs coding for the V-regions. In addition, the PCR primers were designed to introduce a standard Kozak sequence (Kozak (1987) *Nucleic Acids Res.* 15(20): 8125-8148, incorporated by reference herein in its entirety) at the 5'-ends of both the light and heavy chain cDNAs to allow efficient translation, and to introduce splice donor sites at the 3'-ends of both the light and heavy chain cDNAs for the variable regions to be spliced to the constant regions. The PCR primers used for the construction of the chimeric 19/2 light and heavy chains were as follows: catgtttaaacgccfccac-catgggcttcaagatggagtca (5' end, light chain variable region, SEQ ID NO: 31); agaggatccactcacgtttcagttccacttggtcccag (3' end, SEQ ID NO: 32); catgtttaaacgccgccaccatggagct-gatcatgctcttcct (primer for the 5' end of the heavy chain variable region, SEQ ID NO: 33); and agaggatccactcacctgag-gagactctgagagtggt (primer for the 3' end of the heavy chain variable region, SEQ ID NO: 34). The DNA and amino acid sequences of the mouse 19/2 VL and VH regions were adapted for use from the construction of chimeric 19/2 light and heavy chains. The entire DNA sequences of mouse 19/2 light and heavy chains cloned into the eukaryotic expression vectors pREN-Neo and pREN-DHFR, respectively, are set forth as SEQ ID NO: 35 & 36, with the resulting light and heavy chains resulting in chimerized molecules. Specifically, in SEQ ID NO: 35, nucleotides 1357-1756 encode the murine, light chain sequence, with nucleotides 1763-2206 encoding the human kappa region. Within this sequence (1763-2206), a 120 base pair region constituting an intron and splice acceptor site begins at nucleotide 1886. Within SEQ ID NO: 36, nucleotides 1357-1770 encode the murine 9/2 heavy chain constant sequence with a splice donor site. Nucleotides 1777-2833 encode the human IgG1 constant region. Within this sequence, there is a 60 base pair intron region and splice acceptor site which precedes the coding region.

Example 5

The objective of the experiments described herein was to create stable cell lines expressing chimeric 19/2 (c19/2) anti-human GM-CSF monoclonal antibodies (mAb) in CHO (Chinese hamster ovary) DG44 cells and to test the secreted antibody for its binding properties. To do this, the DHFR negative CHO cell line DG044 was used. See Morris et al. (1990) *Gene* 94(2): 289-294; incorporated by reference herein in its entirety). The CHO cells were cultured in RPMI, supplemented with 10% FCS and Hypoxanthine-Thymidine. DNA for transfection was purified from *E. coli* cells using a commercially available product, and the instructions provided therein. All DNA preparations were examined by restriction enzyme digestion. Sequences of chimeric 19/2 mAb variable regions in their respective vectors were confirmed using an ABI PRISM 310 or LICOR Sequencer.

Vectors encoding heavy and light chains of chimeric 19/2 mAbs were co-transfected simultaneously into CHO DG44 cells growing at log phase, using electroporation (270V, 975 uF). Cells were plated in 10 cm dishes and cultured with standard medium. Twenty-four hours later, medium was harvested and replaced by fresh RPMI medium supplemented with 10% dialyzed FCS and 500 ug/mL geneticin. After the initial phase of cell killing was over (7-10 days), GMP-grade methotrexate was added at a concentration of 5 nM and gradually increased to 100 nM over the following weeks. Out-growing colonies were picked and screened for antibody production.

Example 6

PCR Amplification of Variable Chain DNA

CHO DG44 cells were centrifuged in an Eppendorf microcentrifuge, briefly, at full speed, washed once with PBS, and pelleted once again. Genomic DNA was prepared by ethanol precipitation after SDS lysis and Proteinase K treatment of the cell pellets.

A mixture containing one of the primer pairs described supra, dNTPs, buffer, and Pfu polymerase was used to amplify either the heavy or light chain variable region using genomic DNA as a template using methods well known in the art. The resulting PCR products were digested with the appropriate restriction enzyme and analysed by agarose gel electrophoresis to confirm their identity.

The primer pairs for the light chain were:

```
ttcttgaagt ctggtgatgc tgcc,          (SEQ ID NO: 37)
and

caagctagcc ctctaagactc ctcccctgtt.  (SEQ ID NO: 38)
```

For the light chain and SEQ ID NO: 37 plus

```
                                     (SEQ ID NO: 39)
     gaactcgagt catttacccg gagacaggga gag
```

for the heavy chain.

The undigested heavy chain PCR product had a predicted size of 1200 base pairs, while the light chain PCR product had a predicted size of 800 base pairs. Identity was verified by restriction enzyme digest with BamHI.

Example 7

Dot-Blot Method for Measuring Assembled IgG1/Kappa Antibody in CHO Cell Supernatants CHO cell lines were transfected with the corresponding plasmids. Geneticin resistant cells were obtained and these cells were further selected for resistance to methotrexate. Single colonies were picked after amplification and transferred into 24-well plates. Culture supernatant was tested for chimeric IgG 3-4 days later by standard Dot Blot assays.

Figure 2:
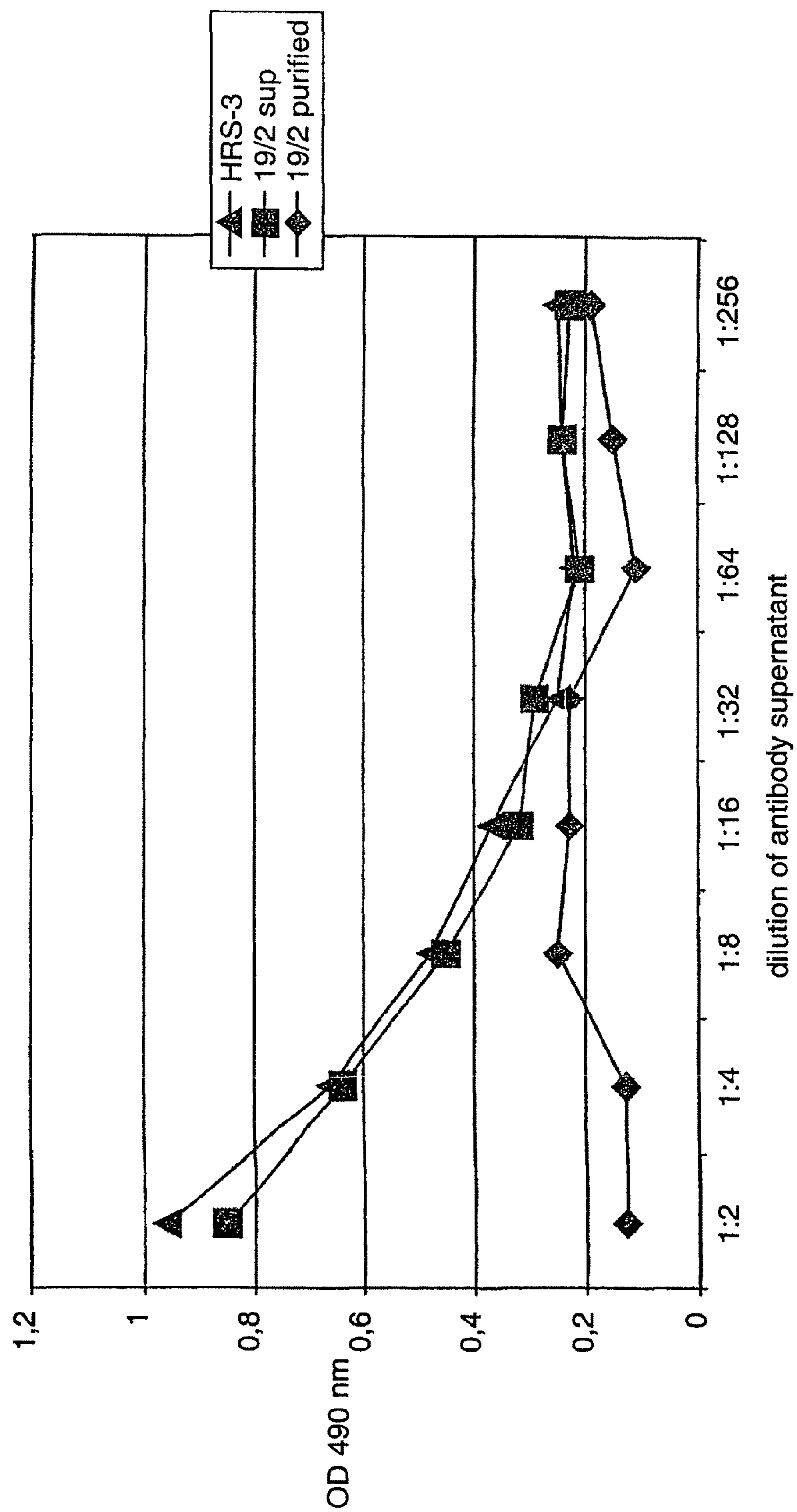
FIG. 2 shows the binding of the antibody via ELISA.

Any positive colonies were sub-cloned and cultured to achieve sufficient antibody production. The chimeric 19/2 antibody was purified from the supernatant on protein G columns and tested for its specific binding with recombinant GM-CSF by Western Blot (FIG. 1) and ELISA (FIG. 2).

Finally, the identity of producer cell lines were confirmed using PCR amplification of both their heavy and light chain variable regions. The DNA sequence of the heavy chain variable region PCR products for chimeric 19/2 mAb transfected cells was confirmed.

Example 8

In order to optimize cell growth and antibody production, the CHODG44/pREN c19/2 cell line was first cultured in commercially available IMDM containing 10% FCS, at 37° C., in a 10% $CO_2$ atmosphere. The cells were then weaned into serum free medium, and cultured in a custom made medium, i.e., IMDM SFII, with the following additives, at 37° C., in a 10% $CO_2$ atmosphere.

| | Final Concentration |
|---|---|
| Base IMDM Medium | |
| Pluronic F68 | 1.0 mg/ml |
| Hypep 4601 | 1.0 mg/ml |
| Hypep 4605 DEV | 0.5 mg/ml |
| HEPES | 5.958 mg/ml |
| $Na_2HCO_3$ | 3.024 mg/ml |
| Additives | |
| Dextran sulfate | 50.0 μg/ml |
| Putrescine | 100.0 nM |
| Albumax I | 2.0 mg/ml |
| Choline chloride | 1.0 mg/ml |
| Trace elements | |
| $FeSO_4 \cdot 7H_20$ | 0.8 μg/ml |
| $ZnSO_4 \cdot 7H_20$ | 1.0 μg/ml |
| $CuSO_4 \cdot 5H_20$ | 0.0025 μg/ml |
| $C_6H_5FeO_7 \cdot H_20$ | 5.0 μg/ml |
| IGF-1 | 50.0 ng/ml |
| Transferrin | 35.0 μg/ml |
| Ethanolamine | 50.0 μM |
| Mercaptoethanol | 50.0 μM |

Culture supernatants were harvested asceptically, and then clarified by centrifugation. The antibodies were then purified by affinity chromatography on a 5 ml protein. A sepharose fast flow column that had been pre-equilibriated in 50 mM Tris-HCL, pH8, was used. The column was washed, 20 times, with this buffer, and any bound antibody was eluted using 50 mM sodium citrate, pH 3.0, and the eluate was then neutralized, immediately, using 1M Tris-HCl, pH8. Antibodies were concentrated with a centrifugal filter, and dialyzed overnight at 4° C. in PBS. The yield was about 4-5 mg/liter. The purity of the antibodies was examined via SDS-PAGE, under both reducing and non-reducing conditions, using a 4-20% gradient on the SDS-PAGE.

Purified antibodies migrated as a single band under non-reducing conditions, and separated into the heavy and light chains, as expected, under reducing conditions.

The antibodies were also analyzed via size exclusion chromatography, (0.5 mg/ml), on a precalibrated HPLC column. Running buffer (5% n-propanol/PBS (0.5 M phosphate, 0/25 M NaCl, pH 7.4)) was used, at a flow rate of 0.2 ml/min at a temperature of 22° C., which is ambient column temperature.

The analysis demonstrated the integrity of the antibodies, which had calculated molecular weights of 179 kilodaltons.

Example 9

The experiments described in this example were designed to determine the binding activity of the antibodies.

Biosensor analyses were carried out using a commercially available, BIAcore 2000, and a carboxymethyldetran coated sensor chip. The chip was derivatized with 1000, 300, or 100 RVs of recombinant human GM-CSF, on channels 1, 2, and 3 of the machine using standard amine coupling chemistry with channel 4 retained as the control blank channel.

Samples of the chimeric antibody were diluted in HBS buffer (10 mM HEPES, pH7.4, 150 mM NaCl, 3.4 mM di-NA-EDTA, 0.005% Tween-20), and aliquots were injected over the sensor chip at a flow rate of 1 μl/min. After injection, dissociation was monitored by allowing HBS buffer to flow over the chip surface for 5 minutes. Any bound antibody was then eluted, and the chip surface was regenerated, between samples, via injecting 40 μl of 100 mM HCl, pH 2.7, at a rate of 5 μl/min. In order to carry out kinetic analyses of the binding of the chimeric antibody, varying concentrations, ranging from 1-10 nM, were injected over the chip surface, and both apparent association ("Ka") and dissociation ("Kd") rate constants were calculated, using a Langmuir 1:1 binding model, with global and local fitting for calculation of Rmax, using B1 Aevaluation V3.1 software.

The results indicated that the chimeric antibody had slightly higher affinity for rhGM-CSF than the murine antibody. The calculated Ka for the chimeric antibody was $5.1\times10^5 M^{-1}s^{-1}$ using 100 RU of GM-CSF. No dissociation was observed, regardless of analyte concentration, precluding Kd determination and indicating very high affinity.

Global fitting of Rmax, using the software referred to, gave an off rate of $Kd=1.9\times10^{-5}s^{-1}$ and a high affinity for the chimeric antibody of $2.69\times10^{10}M^{-1}$.

Example 10

These experiments were designed to determine both the binding activity of the antibodies, and if they cross-reacted with each other.

Nunc plates were coated with recombinant human GM-CSF (1 μg/ml), in carbonate buffer (pH 9.6, 0.05 M), 50 μl/well, and were incubated at 4° C., overnight, and were then blocked with 3% FCS/PBS at room temperature, for one hour.

Half-log, serially diluted triplicate 100 μl samples of either murine or chimeric antibody (10 μg/ml) were added to each well, to yield final concentrations of from 1.0 ng/ml to 10 μg/ml. Following incubation for 1 hour at room temperature, either goat antimouse IgG or antihuman IgG, labelled with horseradish peroxidase (10 ul/well Fc specific; 1:1000 dilution in 1% FCS/PBS) were used to detect bound antibody. After extensive washings, the bound antibodies were visualized by the addition of ABTS substrate (100 μl/well).

Optical density was read at 415 nm in a microplate reader.

The same protocol for binding antibody to the solid phase was used to determine if the antibodies competed with each other. As in the experiments, supra, half-log, serially diluted 100 μl samples, in triplicate, of 10 μg/ml of the murine or chimeric antibody were combined with 20 μg/ml of competing antibody, and then 100 ml of the mixture was added to the coated ELISA plates. Incubation was as above, and anti-murine or anti-human IgG labelled with horseradish peroxidase was used, also as described supra.

The results indicated that the antibodies did compete for binding for recombinant human GM-CSF. A shift in the binding curve was effected by addition of the excess, competing antibody. This indicated binding to, and competition for, a common epitope.

Example 11

These experiments were designed to test the neutralizing activity of the anti-GM-CSF antibodies. Two human GM-CSF dependent cell lines, i.e., TF-1 and AML-193 were used. Growth curves were established, in the presence or absence of 0.5 ng/ml of recombinant human GM-CSF, and viable cell numbers were determined, via Trypan Blue exclusion, on day 0, 1, 2, 3, 5 and 7.

In a first bioassay, recombinant human GM-CSF, in amounts ranging from 0.0003 ng/ml up to 10 μg/ml, was mixed with anti-human GM-CSF antibodies, at a final concentration of 30 μg/ml, in 96 well, microtitre plates. Either TF-1 or AML-193 cells were added ($10^3$ cells/well), and plates were incubated at 37° C. for 7 days.

After this incubation period, the DNA proliferation marker MTS was added, at 20 μl/well. Dye incorporation was measured after 2 hours, by measuring light absorbance at $A_{490\ nm}$.

Increased MTS dye incorporation was observed as the amount of rhGM-CSF in the medium increased. Total growth inhibition of both cell types was observed with the chimeric antibody when rhGM-CSF concentration was 0.1 ng/ml or less, and there was marked inhibition of cell growth at 0.3-10 ng/ml rhGM-CSF.

Figure 3:
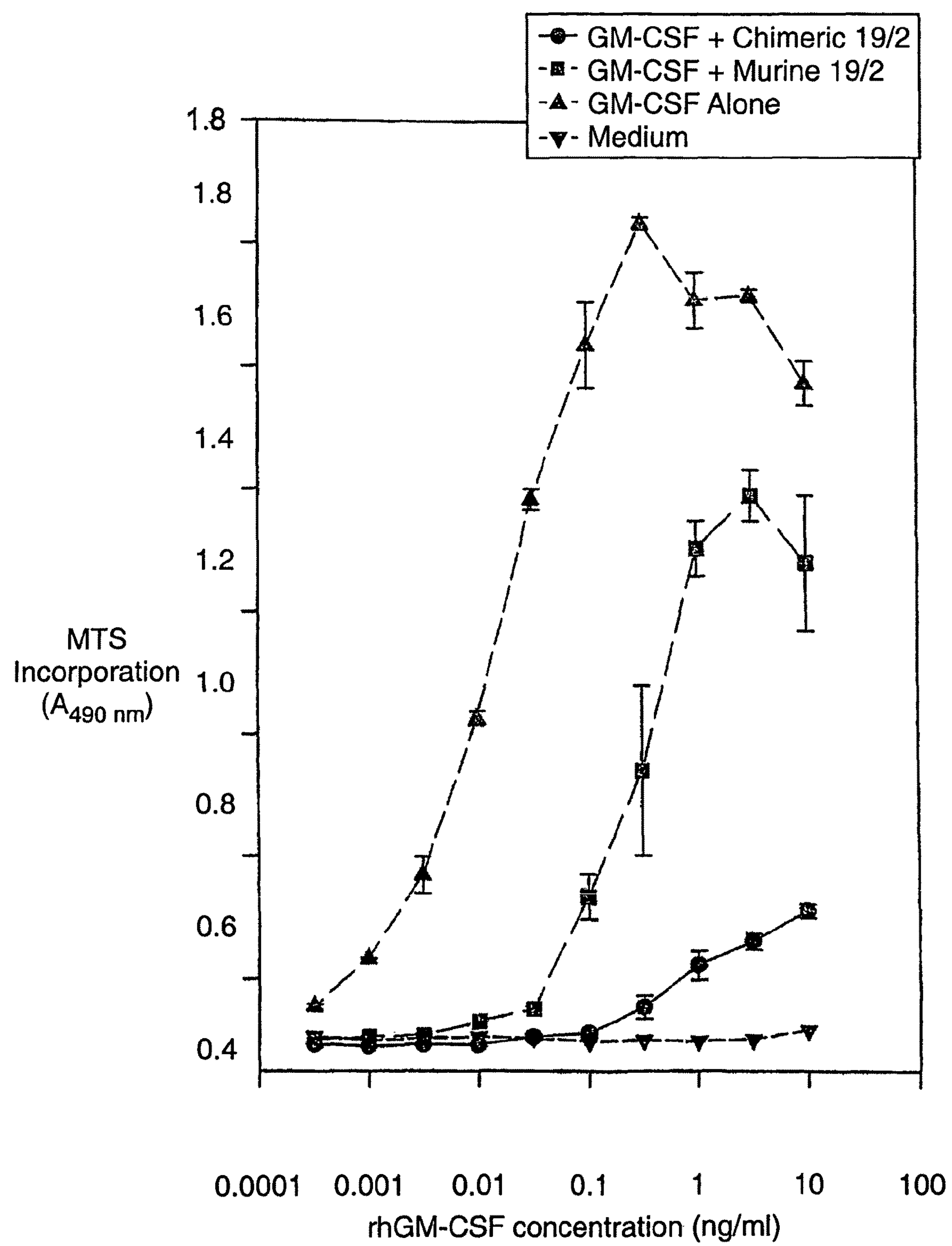
FIG. 3 shows the blocking effect of the antibody on GM-CSF growth dependent TF-1 cells.
Figure 4:
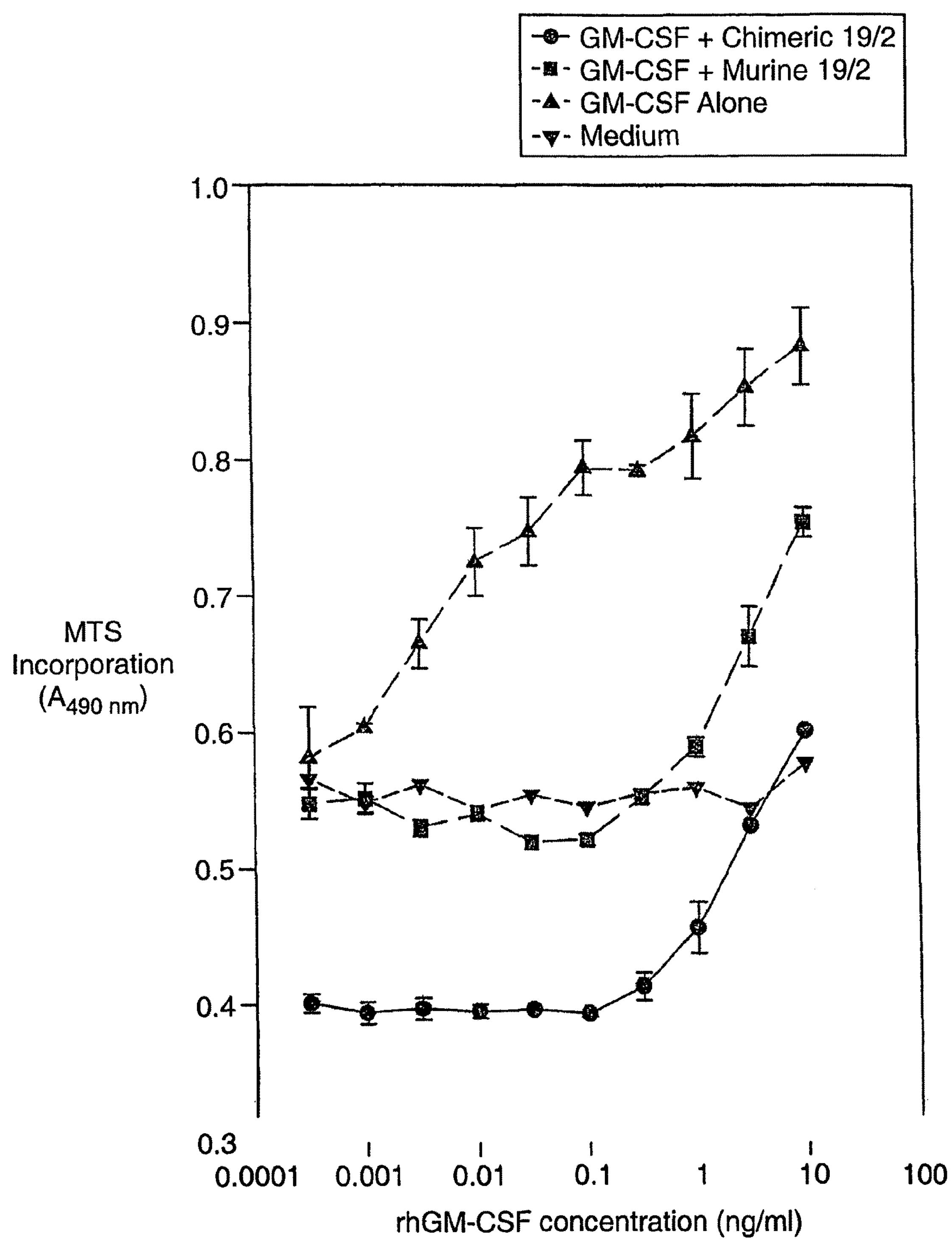
FIG. 4 shows the blocking effect of the antibody on GM-CSF growth dependent AML-193 cells.

In contrast, while the murine antibody had a similar effect on AML-193 cells, it was less effective on TF-1 cells. These results are seen in FIGS. 3 and 4.

Figure 5:
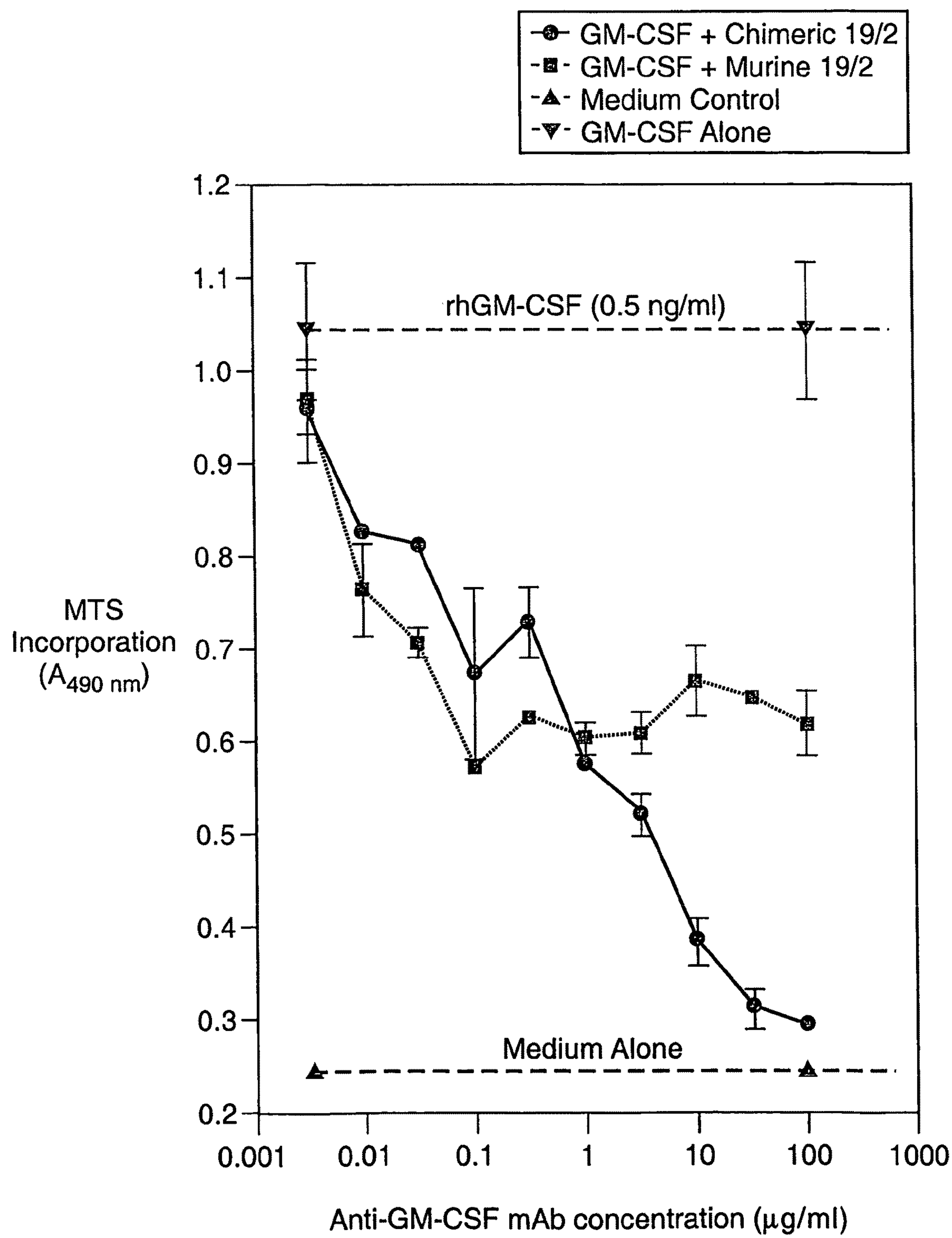
FIG. 5 shows results of an assay testing the effect of increasing concentration of murine or chimeric 19/2 mAbs, on TF-1 cells grown in the presence of a constant amount of human GM-CSF.
Figure 6:
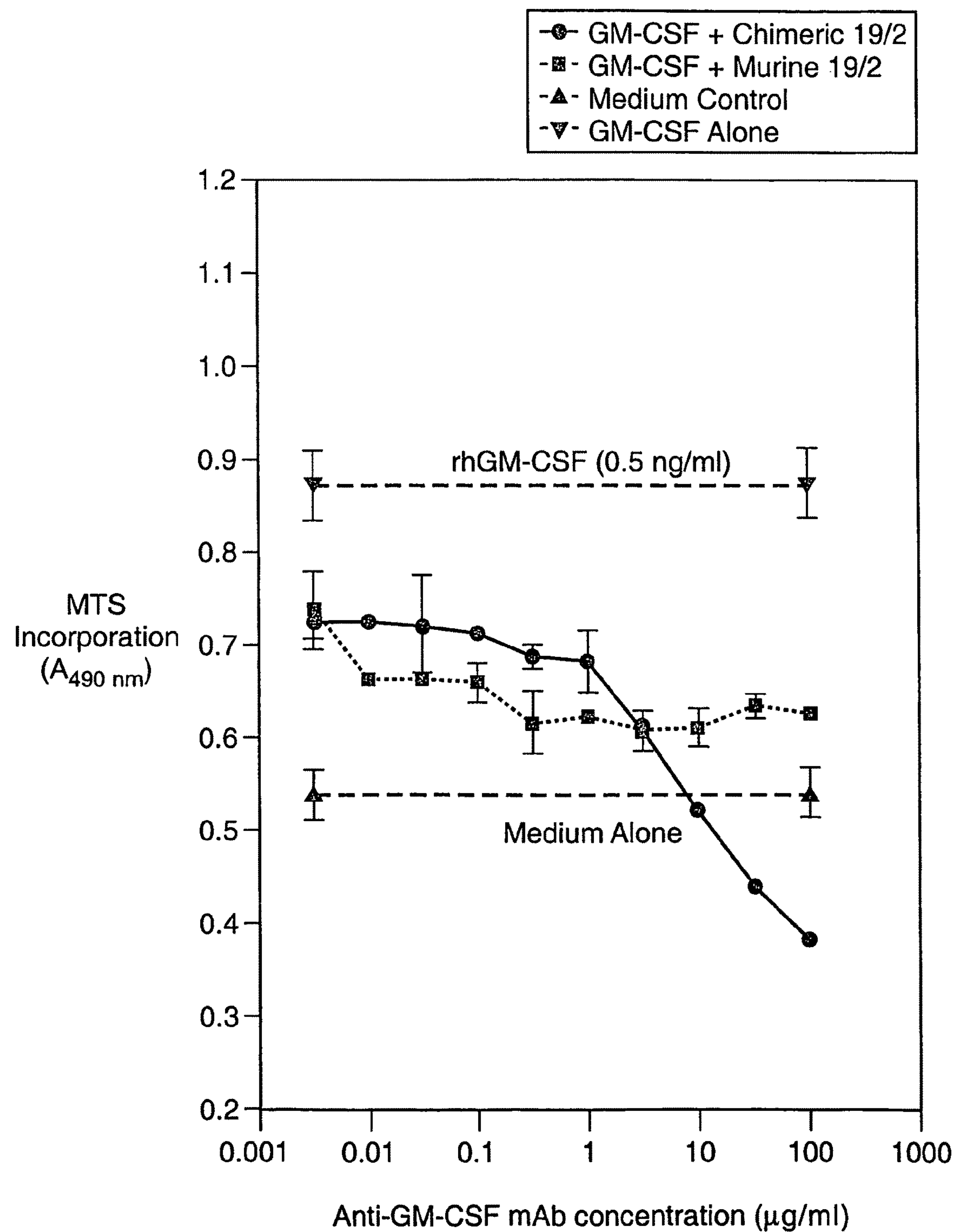
FIG. 6 parallels the experiment of FIG. 5, but uses the AML-153 cells.
Figure 7A:
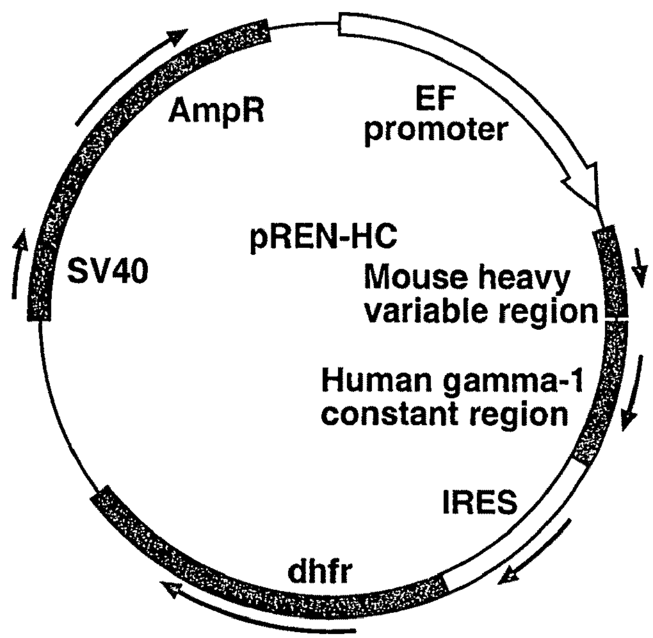
FIG. 7 shows a schematic map of the two expression vectors used to prepare the recombinant antibodies.
Figure 7A:
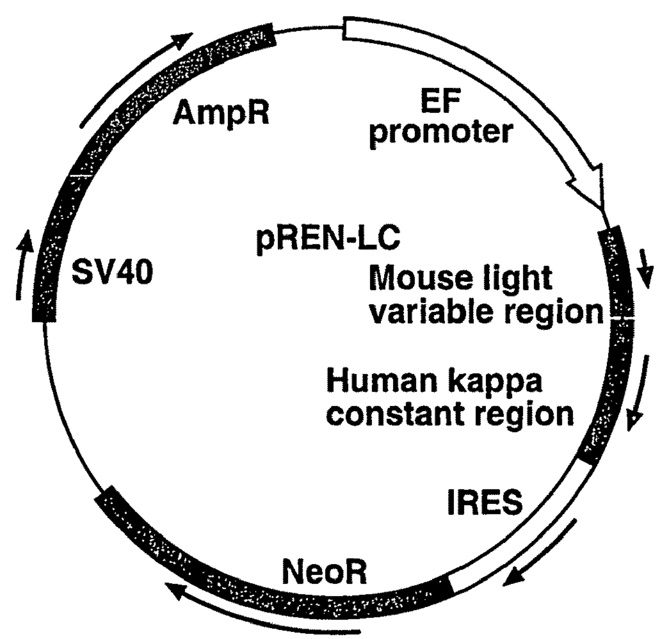

In a second bioassay TF-1 and AML-193 cells were grown in the presence of 0.5 ng/mL rhGM-CSF and increasing amounts of murine or chimeric 19/2 mAbs (0.003-100 μg/mL) were added to the culture media and the neutralizing activity assessed after 7 days culture. Results are shown in FIGS. 5 and 6 for the TF-1 and AML-193 cells, respectively. In agreement with the initial bioassay, the chimeric 19/2 demonstrated marked neutralizing activity of GM-CSF stimulated cell growth. A direct correlation was observed between increasing ch19/2 concentration and GM-CSF neutralizing activity plateaued at 3 μg/mL for both cell lines, with higher concentrations unable to effect a greater reduction in TF-1 or AML-193 cell growth. These observations may be due to lower affinity of the murine mAb or steric hindrance at the binding site on GM-CSF.

Example 12

Additional experiments were carried out to produce a chimeric, HRS-3 antibody. The murine form of this antibody is described by Hombach, et al, Int. J. Cancer 55:830-836 (1993), incorporated by reference. The murine antibody binds to CD-30 molecules.

The protocols set forth for production of chimeric, anti GM-CSF antibody set forth supra were used. Since the antibodies were different, and sequences were known, however, different primers were used. These primers serve to introduce splice sites into the cDNA sequences encoding the murine heavy chain and light chain variable regions, and are set forth at SEQ ID NOS: 44, 45, 46 & 47, with SEQ ID NOS: 44 & 45 the nucleotide and amino acid sequences of the heavy chain, and 46 & 47 comparable sequences for the light chain The primers were:

```
                                  (SEQ ID NO: 40)
gcgccatggc ccaggtgcaa ctgcagcagt ca
and

                                  (SEQ ID NO: 41)
cagggatcca ctcacctgag gagacggtga ccgt,

and for the light chain:
                                  (SEQ ID NO: 42)
agcgccatgg acatcgagct cactcagtct cca
and

                                  (SEQ ID NO: 43)
cagggatcca actcacgtttg atttccagct tggt.
```

Following amplification, the murine heavy and light chain variable regions were cloned into the pREN Neo and pREN-DHFR sequences, which are set forth at SEQ ID NOS: 48 & 49, respectively. The cloning was possible because the amplification introduced PmeI and BamHI restriction sites into SEQ ID NO: 44, at nucleotides 1-7, and the final 6 nucleotides. Comparable sites are found at nucleotides 1340-1348, and 1357-1362 of SEQ ID NO: 48. Similarly, PmeI and BamHI restriction sites were introduced at nucleotides 1-8, and the last 6 nucleotides of SEQ ID NO: 47, such that this nucleotide sequence could be cloned into SEQ ID NO: 49, at positions 1337-1344, and 1349-1354.

The chimeric HRS-3 antibody was designed to have murine HRS-3 VL and VH regions linked to human kappa and gamma-1 constant regions, respectively. PCR primers were used to modify the 5'- and 3'-sequences flanking the cDNA sequences coding for the murine HRS-3 VL and VH regions. Modification included the insertion of a NcoI site at the 5' primer end and a splice donor site followed by a BamHI restriction site at the 3'-end of both the light and heavy chain cDNAs for the variable regions to be spliced to the constant regions. These adapted mouse HRS-3 variable regions were then subcloned through the NcoI/BamHI restriction sites into a prokaryotic vector harboring a 5'PmeI site followed by a 5' Kozak sequence and by a human antibody leader sequence. Sequences were cut from the prokaryotic vector by PmeI/BamHI digest and subcloned into mammalian cell expression vectors already containing the human kappa (pREN-Neo vector) or gamma-1 (pREN-DHFR vector) constant regions, described supra.

Example 13

Once the constructs were established, they were transfected into DG044 cells, as described supra.

Positive colonies were sub-cloned, cultured to achieve sufficient antibody production, after which the antibodies were purified, on protein G columns via the Fc fragment.

The purified antibodies were analyzed via SDS-PAGE, following Laemmli, Nature 227:680-5 (1970), as modified by Renner, et al, Eur. J. Immunol. 25:2027-35 (1995), incorporated by reference. Samples from different stages of purification were diluted, in either reducing or non-reducing buffer, and were separated on 10-12% polyacrylamide gel via electrophoreses followed by standard Coomassic staining.

The results were in accordance with production of a complete, chimeric antibody, as evidenced by the banding patterns found in both reducing and non-reducing solutions.

Example 14

The binding capacity of the chimeric HRS-3 antibody was determined via flow cytometry, in accordance with Renner, et al, supra. In brief, $1\times10^6$ cells of a target tumor line which expressed CD-30 were washed, twice, in PBS, and then incubated with varying concentration of antibody, at 4° C., for 30 minutes. The cells were then washed, and incubated with a secondary antibody, which was directed to the light chain, conjugated to either FITC or PE.

The results indicated that there was weak binding from cell culture supernatant purified from transfected CHO cells, and string binding with purified antibody. No binding was found when CD-30 negative tumor cells were used.

Example 15

The antibody dependent cellular toxicity (ADCC), and the complement dependent toxicity of the chimeric HRS-3 antibody were determined using a europium released assay, as described by Hombach, et al, supra, and Renner, et al, supra.

In brief, for the ADCC assay, peripheral blood lymphocytes were isolated from tow healthy donors, and used at an effector:target ratio of 10:1, with 10,000 europium labelled, CD-30 antigen positive L540CY tumor cells. Antibody was added at varying concentrations (10 μl, 0.1 and 0.01 μg/ml), as was a control of 0 μg/ml. The effect was compared to the murine antibody, a bispecific murine anti-CD16/CD30 antibody, and an irrelevant, chimeric IgG1 antibody. A CD30 negative line was also used. Maximum lysis was measured after 0.025% Triton was added, and all assays were carried out in triplicate.

The results indicated that the chimeric antibody performed better in the ADCC than the murine antibody.

In the CDC assays, 10,000 europium labelled cells (100 μg) (L540Y), were incubated, with 50, 5, 0.5, or 0.05 μg/ml antibody in a 500 volume. Freshly isolated complement (50 μl) was added, and the mixture was incubated for 2 hours, at 37° C. The murine antibody was also tested, as was an anti CD-16 antibody and a chimeric anti IgG antibody, which served as controls, as did a CD-30 negative cell.

As in the ADCC assay the chimeric antibody was superior in terms of percent lysis to all other antibodies tested.

Example 16

This example details the production of a fusion protein of a chimeric, G250 specific antibody, and tumor necrosis factor ("TNF" hereafter).

G250 is an antigen also now as "carbonic anhydrase 9," or "CA9," or "MN." The G250 antigen and the corresponding antibody was described as being associated with renal cancer carcinoma by Oosterwijk, et al, PCT/US88/01511. The G250 antibody has also been the subject of several clinical trials (Oosterwijk, et al., Int. J. Cancer 1986: Oct. 15, 38(4):489-494; Divgi, et al., Clin. Cancer Res. 1998: Nov 4(11):2729-739.

Zavada, et al, have issued a series of patents in which the G250 antigen is referred to as "MN" or "MN/CAIX." See, e.g., U.S. Pat. Nos. 6,051,226; 6,027,887; 5,995,075, and 5,981,711, all of which are incorporated by reference. These parents provide details on the antigen, and describe various tumors in which it is found, including cervical cancer, bladder cancer, mammary carcinoma, uterine, cervical, ovarian, and endometrial cancer.

Recently, Ivanov, et al, Am. Journal of Pathology 158(3): 905-919 (2001), conducted investigations of CA9 and CA12 on tumor cells, and cell lines.

cDNA sequences for the light and heavy variable regions of a murine G250 specific antibody are known, and these include the endogenous antibody leader sequence.

PCR primers were used to modify both the 5' and 3' regions, in order to introduce restriction sites necessary for the introduction of the coding sequences to the vectors employed, which were SEQ ID NOS: 48 & 49, supra. The cDNA sequence which encodes the murine G250 heavy chain variable region is set forth at SEQ ID NO: 50, with the amino acid sequence at SEQ ID NO: 51 and the light chain variable region, at SEQ ID NO: 52, with amino acid sequence at SEQ ID NO: 53. The first 8 nucleotides in each of SEQ ID NOS 50 & 52 represent a PmeI restriction site. The first 19 amino acids encoded by the nucleotide sequence represent the leader region, and the first 24 the leader sequence for the light chain. The last 6 nucleotides in each of SEQ ID NOS: 50 & 52 are a BamHI restriction site. The same protocol as was used for the HRS-3 chimera was used to splice these variable regions into SEQ ID NOS: 46 & 47.

To secure the cDNA encoding human TNF, a human leukocyte cDNA library was used. The peripheral blood lymphocytes were stimulated with PMA, and the cDNA for TNF was amplified, using standard methods. Restriction sites were introduced in the cDNA sequence, so that the cDNA for TNF was positioned right after the hinge region of the G250 heavy chain. A (Gly) Ser coding sequence linked the two. SEQ ID NOS: 54 & 55 set forth the nucleotide and amino acid sequences of a TNF fragment, and SEQ ID NO: 56, a construct wherein the human gamma-1 heavy chain is followed by the TNF coding sequence, right after the IgG1 hinge region.

Within SEQ ID NO: 56, nucleotides 1419-1754 encode a partial, human IgG1 constant region, containing the CH1 and hinge domain, preceded by a 60 base pair intron region and splice acceptor site. The linker, i.e., $(Gly)_4$Ser is encoded by nucleotides 1755-1769. The coding sequence for the human TNF fragment is set forth at nucleotides 1776-2296.

The resulting constructs were transfected into host cells, as described supra, and expressed. Note that SEQ ID NO: 56 contains a variant of the heavy chain vector noted supra, as it contains the human CH1 and hinge regions, followed by the TNF encoding sequence.

Cells were transfected and cultured as described supra for the HRS-3 chimera, and amplification was carried out using the primers of SEQ ID NOS: 40-43, described supra. The predicted size of the amplification product was 1100 base pairs, and this was in fact confirmed.

Positive colonies were then sub-cloned and cultured, as described supra. The chimeric G250-TNF fusion proteins were purified using anion exchanged chromatography on DEAE columns, using 5 ml samples, and increased salt concentrations in the elution buffer (NaCl, 0→0.5 M) (pH 8). The purity of the fusion proteins was determined, on SDS-PAGE, under reducing conditions. Two bands, of 45 and 28 kDa, respectively, appeared, consistent with the production of a chimeric fusion protein.

The purity of the chimeric fusion protein was confirmed in a sandwich ELISA. In brief, plates were coated with 1:6000 dilutions of affinity purified, goat anti-human IgG serum, and incubated overnight. They were then blocked with 2% gelatin. Either cell culture supernatant, or purified antibody was added, at varying concentrations, and then contacted with biotinylated goat anti-human TNFα specific serum, at 0.1 μg/ml, followed by visualization with a standard streptavidin peroxidase reagent.

The ELISA confirmed the purity of the antibody.

Example 17

FACS was carried out, as described supra for the chimeric HRS-3 antibodies, this time using the fusion protein, and G250 positive tumor cells. Two different purification runs were tested, with chimeric G250 antibody as a positive control, and an irrelevant chimeric IgG1 antibody as a negative control.

The results indicated that the chimeric fusion protein bound as well as the chimeric antibody did. No binding was detected when G250 negative cells were used.

Example 18

These experiments were designed to determine if the fusion proteins retained the ability of TNF to mediate cell death.

This was accomplished using an MTT assay as described by Renner, et al, Eur. J. Immunol. 25:2027-2035 (1995), incorporated by reference, and TNF sensitive ("WEHI-R") cells. The WEHI cells were seeded at a density of 10,000 cells/well. Then, after 18 hours, sterile samples of the fusion protein, recombinant TNF, chimeric G250 antibody, or a negative control (plain medium), were added, at concentrations of $1.0\times10^5$, $1.0\times10^2$, 1, $1.0\times10^{-2}$, $1.0\times10^{-4}$, and 1.0×

$10^{-5}$ ng/ml, and the culture was incubated for additional period of from 48-72 hours. Any viable cells were detected, via standard methods, including Annexin V staining, and flow cytometry. To do this, $1\times10^{6}$ WEHI cells were incubated, overnight, with varying antibody concentrations, and dye positive cells were counted. The effect of antibody loaded tumor cells in WEHI killing was determined by pre-staining with commercially available PKH-26GL dye.

The chimeric fusion proteins were found to be as effective as recombinant TNF in killing cells.

Example 19

It is known that TNF stimulates $H_2O_2$ release by human leukocytes. The chimeric fusion proteins were tested for this property.

Granulocytes were isolated from blood samples via standard methods, and were resuspended in reaction buffer (KRPG=145 mM NaCl, 5 mM $Na_2HPO_4$, 4.8 mM KCl, 0.5 mM $CaCl_2$, 1.2 mM $MgSO_4$, 0.2 mM glucose, pH 7.35). This mix was added plates that had been precoated with fibronectin (1 μg/ml, 2 hours, 37° C.) to permit granulocyte adherence. Following this, 100 μl of a dye solution (10 ml KRPG+50 μl A6550+10 μl horseradish-peroxidase) were added and incubated for 15 minutes at 37° C. Granulocytes were added, at 30,000 cells per well, and then either buffer (KRPG), PMA (5 ng/ml), the chimeric fusion protein (1 μg/ml) plus recombinant human IFN-γ (100 μ/ml), or the fusion protein plus the recombinant IFN-γ (at the indicated concentrations), were added. $H_2O_2$ release was measured for 3 hours, using standard methods.

The PMA served as a positive control. The chimeric fusion protein induced $H_2O_2$ release significantly higher than antibody alone, and the $H_2O_2$ release increases even more when IFN-γ was added.

We claim:

1. An isolated nucleic acid molecule which encodes a chimerized, GM-CSF specific antibody light chain, the amino acid sequence of which consists of the amino acid encoded by nucleotides 1357-1752 of SEQ ID NO: 35, concatenated to the amino acid sequence encoded by nucleotides 1886-2203 of SEQ ID NO: 35.

2. An isolated nucleic acid molecule which encodes a chimerized, GM-CSF specific antibody heavy chain, the amino acid sequence of which consists of the amino acid encoded by nucleotides 1357-1764 of SEQ ID NO: 36, concatenated to the amino acid sequence encoded by nucleotides 1839-2825 of SEQ ID NO: 36.

3. An expression vector which comprises the isolated nucleic acid molecule of claim 1, operably linked to a promoter.

4. An expression vector which comprises the isolated nucleic acid molecule of claim 2, operably linked to a promoter.

5. An expression vector of claim 3, consisting of the nucleotide sequence of SEQ ID NO: 35.

6. An expression vector of claim 4, consisting of the nucleotide sequence of SEQ ID NO: 36.

7. A recombinant cell, transformed or transfected with the isolated nucleic acid molecule of claim 1.

8. A recombinant cell, transformed or transfected with the isolated nucleic acid molecule of claim 2.

9. The isolated nucleic acid molecule of claim 1 comprising nucleotides 1357-1752 and 1886-2203 of SEQ ID NO: 35.

10. The isolated nucleic acid molecule of claim 2 comprising nucleotides 1357-1764 and 1839-2825 of SEQ ID NO: 36.

11. A recombinant cell transformed or transfected with the expression vector of claim 3.

12. A recombinant cell transformed or transfected with the expression vector of claim 4.

* * * * *